US007732375B2

(12) United States Patent
Dunkel et al.

(10) Patent No.: US 7,732,375 B2
(45) Date of Patent: Jun. 8, 2010

(54) HEXYL CARBOXANILIDES AND THEIR USE FOR CONTROLLING FUNGI

(75) Inventors: Ralf Dunkel, Lyons (FR); Hans-Ludwig Elbe, Wuppertal (DE); Olaf Gebauer, Leverkusen (DE); Jörg Nico Greul, Leichlingen (DE); Benoit Hartmann, Langenfeld (DE); Ulrike Wachendorff-Neumann, Neuwied (DE); Peter Dahmen, Neuss (DE); Karl-Heinz Kuck, Langenfeld (DE)

(73) Assignee: Bayer CropScience AG, Monheim (DE)

( * ) Notice: Subject to any disclaimer, the term of this patent is extended or adjusted under 35 U.S.C. 154(b) by 400 days.

(21) Appl. No.: 10/576,243

(22) PCT Filed: Oct. 12, 2004

(86) PCT No.: PCT/EP2004/011397

§ 371 (c)(1),
(2), (4) Date: Oct. 27, 2006

(87) PCT Pub. No.: WO2005/042493

PCT Pub. Date: May 12, 2005

(65) Prior Publication Data

US 2007/0037858 A1    Feb. 15, 2007

(30) Foreign Application Priority Data

Oct. 23, 2003 (DE) ................. 103 49 499
Nov. 7, 2003 (DE) ................. 103 52 082

(51) Int. Cl.
    A01N 43/56    (2006.01)
    C07D 231/12    (2006.01)
(52) U.S. Cl. ............... 504/280; 514/406; 548/374.1
(58) Field of Classification Search ......... 504/280; 514/406; 548/374.1
    See application file for complete search history.

(56) References Cited

U.S. PATENT DOCUMENTS

| 5,223,526 | A | 6/1993 | McLoughlin et al. | 514/406 |
|---|---|---|---|---|
| 5,330,995 | A | 7/1994 | Eicken et al. | 514/355 |
| 5,416,103 | A | 5/1995 | Eicken et al. | 514/355 |
| 5,438,070 | A | 8/1995 | Eicken et al. | 514/403 |
| 5,480,897 | A | 1/1996 | Eicken et al. | 514/365 |
| 5,556,988 | A | 9/1996 | Eicken et al. | 548/374.1 |
| 5,589,493 | A | 12/1996 | Eicken et al. | 514/355 |
| 5,747,518 | A | 5/1998 | Yoshikawa et al. | 514/403 |
| 5,922,732 | A | 7/1999 | Urch et al. | 514/304 |
| 5,968,947 | A | 10/1999 | Urch et al. | 514/299 |
| 6,093,726 | A | 7/2000 | Urch et al. | 514/299 |
| 6,174,894 | B1 | 1/2001 | Urch et al. | 514/299 |
| 6,177,442 | B1 | 1/2001 | Urch et al. | 514/299 |
| 6,207,676 | B1 | 3/2001 | Urch et al. | 514/304 |
| 6,239,282 | B1 | 5/2001 | Katsuta et al. | 548/200 |
| 6,291,474 | B1 | 9/2001 | Brightwell et al. | 514/299 |
| 6,331,634 | B1 | 12/2001 | Katsuta et al. | 548/200 |
| 6,331,639 | B2 | 12/2001 | Katsuta et al. | 549/69 |
| 6,365,620 | B2 | 4/2002 | Eberle et al. | 514/422 |
| 6,391,883 | B1 | 5/2002 | Urch et al. | 514/255 |
| 6,573,275 | B1 | 6/2003 | Urch et al. | 514/304 |
| 7,358,214 | B2* | 4/2008 | Dunkel et al. | 504/280 |
| 2001/0023295 | A1 | 9/2001 | Katsuta et al. | 549/76 |
| 2002/0019541 | A1 | 2/2002 | Eberle et al. | |
| 2002/0061913 | A1 | 5/2002 | Urch et al. | |
| 2004/0138265 | A1 | 7/2004 | Walter et al. | |
| 2004/0204470 | A1* | 10/2004 | Elbe et al. | 514/406 |
| 2005/0119130 | A1 | 6/2005 | Walter | |
| 2006/0189676 | A1 | 8/2006 | Walter | |
| 2007/0066673 | A1* | 3/2007 | Dunkel et al. | 514/406 |
| 2007/0072930 | A1* | 3/2007 | Dunkel et al. | 514/406 |

FOREIGN PATENT DOCUMENTS

| CA | 2106497 | 3/1994 |
|---|---|---|
| DE | 10136065 A1 * | 2/2003 |
| WO | 02/059086 | 8/2002 |
| WO | 03/010149 | 2/2003 |

OTHER PUBLICATIONS

STN preliminary search report-10576243.*
Patani et al., Chem. Rev., 1996, vol. 96, p. 3147-3176.*

* cited by examiner

*Primary Examiner*—Yong Chu
(74) *Attorney, Agent, or Firm*—Richard E. L. Henderson

(57) ABSTRACT

The invention relates to novel hexylcarboxanilides of the formula (I)

$$\underset{H_3C}{\overset{O}{\underset{R^1}{\overset{\|}{A-C-N-L}}}}\underset{CH_3}{\overset{R^3}{\underset{\|}{C}-CH_3}}$$

(I)

in which L, $R^1$, $R^3$ and A are as defined in the disclosure, to a plurality of processes for preparing these compounds and their use for controlling unwanted microorganisms, and to novel intermediates and their preparation.

7 Claims, No Drawings

HEXYL CARBOXANILIDES AND THEIR USE FOR CONTROLLING FUNGI

The present patent application has been filed under 35 U.S.C. 371 as a national stage application of PCT/EP2004/011397, filed Oct. 12, 2004, which was published in German as International Patent Publication WO 2005/042493 on May 12, 2005, and is entitled to the right of priority of German Patent Applications 10349499.5, filed Oct. 23, 2003, and 10352082.1, filed Nov. 7, 2003.

The present invention relates to novel hexylcarboxanilides, to a plurality of processes for their preparation and to their use for controlling unwanted microorganisms.

It is already known that numerous carboxanilides have fungicidal properties (cf., for example, WO 03/010149, WO 02/059086, WO 02/38542, WO 00/09482, EP-A0 591 699, EP-A 0 589 301 and EP-A 0 545 099). Thus, for example, 5-fluoro-1,3-dimethyl-N-[2-(1,3,3-trimethylbutyl)phenyl]-1H-pyrazole-4-carboxamide is known from WO 03/010149, N-allyl-N-[2-(1,3-dimethylbutyl)phenyl]-1-methyl-3-(trifluoromethyl)-1H-pyrazole-4-carboxamide is known from WO 02/059086 and N-[2-(1,3-dimethylbutyl)phenyl]-1-methyl-4-(trifluoromethyl)-1H-pyrrole-3-carboxamide is known from WO 02/38542. The activity of these compounds is good; however, at low application rates it is sometimes unsatisfactory.

This invention now provides novel hexylcarboxanilides of the formula (I)

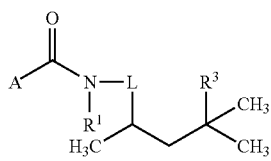

(I)

in which

L represents

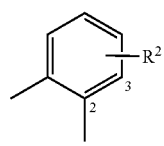

L-1

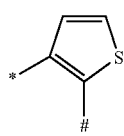

L-2

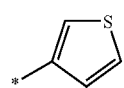

L-3

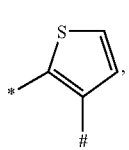

L-4 where the bond marked with * is attached to the amide, whereas the bond marked with # is attached to the alkyl side chain, $R^1$ represents hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-$C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^4$, —CONR$^5$R$^6$ or —CH$_2$NR$^7$R$^8$, $R^2$ represents hydrogen, fluorine, chlorine, methyl or trifluoromethyl, $R^3$ represents halogen, $C_1$-$C_8$-alkyl or $C_1$-$C_8$-haloalkyl, $R^4$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^5$ and $R^6$ independently of one another each represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$alkyl, $C_3$-$C_8$-halocycloalkyl having in each case 1 to 9 fluorine, chlorine and/or bromine atoms, $R^5$ and $R^6$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and NR$^9$, $R^7$ and $R^8$ independently of one another represent hydrogen, $C_1$-$C_8$-alkyl, $C_3$-$C_8$cycloalkyl; $C_1$-$C_8$-haloalkyl, $C_3$-$C_8$-halocycloalkyl having in each case 1 to 9 fluorine, chlorine and/or bromine atoms, $R^7$ and $R^8$ furthermore together with the nitrogen atom to which they are attached form a saturated heterocycle having 5 to 8 ring atoms which is optionally mono- or polysubstituted by identical or different substituents from the group consisting of halogen and $C_1$-$C_4$-alkyl, where the heterocycle may contain 1 or 2 further non-adjacent heteroatoms from the group consisting of oxygen, sulphur and NR$^9$, $R^9$ represents hydrogen or $C_1$-$C_6$-alkyl, A represents the radical of the formula (A1)

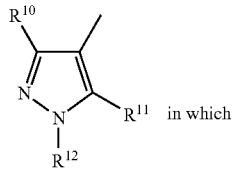

(A1)

in which $R^{10}$ represents hydrogen, hydroxyl, formyl, cyano, fluorine, chlorine, bromine, nitro, $C_1$-$C_4$-alkyl, $C_1$-$C_4$- alkoxy, $C_1$-$C_4$-alkylthio, $C_3$-$C_6$-Cycloalkyl, $C_1$-$C_4$-haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl, $R^{11}$ represents hydrogen, chlorine, bromine, iodine, cyano, $C_1$-$C_4$-alkyl, $C_1$-$C_4$-alkoxy, $C_1$-$C_4$-alkylthio, $C_1$-$C_4$-haloalkyl or $C_1$-$C_4$-haloalkylthio having in each case 1 to 5 halogen atoms, and $R^{12}$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or represents phenyl, or A represents the radical of the formula (A2)

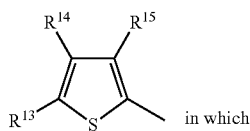
(A2)

in which $R^{13}$ and $R^{14}$ independently of one another represent hydrogen, halogen, $C_1$-$C_4$-alkyl or $C_1$-$C_4$-haloalkyl having in each case 1 to 5 halogen atoms and $R^{15}$ represents halogen, cyano or $C_1$-$C_4$-alkyl, or $C_1$-$C_4$-haloalkyl or $C_1$-$C_4$-haloalkoxy having in each case 1 to 5 halogen atoms, or A represents the radical of the formula (A3)

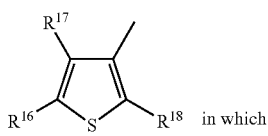
(A3)

in which $R^{16}$ and $R^{17}$ independently of one another represent hydrogen, halogen, $C_1$-$C_4$-alkyl or $C_1$-$C_4$-haloalkyl having 1 to 5 halogen atoms and $R^{18}$ represents hydrogen, $C_1$-$C_4$-alkyl or $C_1$-$C_4$-haloalkyl having 1 to 5 halogen atoms, or A represents the radical of the formula (A4)

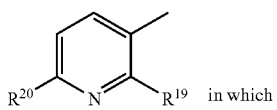
(A4)

in which $R^{19}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms and $R^{20}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulphinyl or $C_1$-$C_4$-alkylsulphonyl, or A represents the radical of the formula (A5)

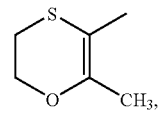
(A5)

or

A represents the radical of the formula (A6)

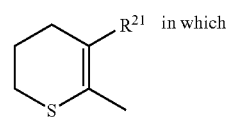
(A6)

in which $R^{21}$ represents $C_1$-$C_4$-alkyl or $C_1$-$C_4$-haloalkyl having 1 to 5 halogen atoms, or A represents the radical of the formula (A7)

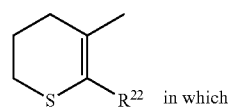
(A7)

in which $R^{22}$ represents $C_1$-$C_4$-alkyl or $C_1$-$C_4$-haloalkyl having 1 to 5 halogen atoms, or A represents the radical of the formula (A8)

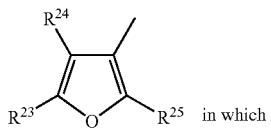
(A8)

in which $R^{23}$ and $R^{24}$ independently of one another represent hydrogen, halogen, amino, $C_1$-$C_4$-alkyl or $C_1$-$C_4$-haloalkyl having 1 to 5 halogen atoms and $R^{25}$ represents hydrogen, $C_1$-$C_4$-alkyl or $C_1$-$C_4$-haloalkyl having 1 to 5 halogen atoms, or A represents the radical of the formula (A9)

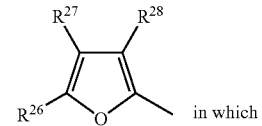
(A9)

in which $R^{26}$ and $R^{27}$ independently of one another represent hydrogen, halogen, amino, nitro, $C_1$-$C_4$-alkyl or $C_1$-$C_4$-haloalkyl having 1 to 5 halogen atoms and $R^{28}$ represents halogen, $C_1$-$C_4$-alkyl or $C_1$-$C_4$-haloalkyl having 1 to 5 halogen atoms, or A represents the radical of the formula (A10)

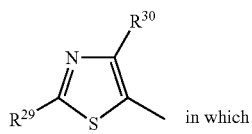
(A10)

in which $R^{29}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms and $R^{30}$ represents halogen, hydroxyl, $C_1$-$C_4$-alkyl, $C_1$-$C_4$-alkoxy, $C_3$-$C_6$-cycloalkyl, $C_1$-$C_4$-haloalkyl or $C_1$-$C_4$-haloalkoxy having in each case 1 to 5 halogen atoms, or A represents the radical of the formula (A11)

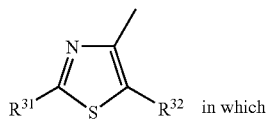
(A11)

in which $R^{31}$ represents hydrogen, halogen, amino, $C_1$-$C_4$-alkylamino, di-($C_1$-$C_4$-alkyl)amino, cyano, $C_1$-$C_4$-alkyl or $C_1$-$C_4$-haloalkyl having 1 to 5 halogen atoms and $R^{32}$ represents halogen, $C_1$-$C_4$-alkyl or $C_1$-$C_4$-haloalkyl having 1 to 5 halogen atoms, or A represents the radical of the formula (A12)

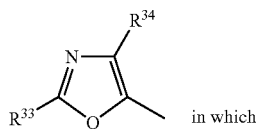
(A12)

in which $R^{33}$ represents hydrogen or $C_1$-$C_4$-alkyl and
$R^{34}$ represents halogen or $C_1$-$C_4$-alkyl, or A represents the radical of the formula (A 13)

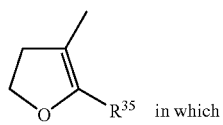
(A13)

in which $R^{35}$ represents $C_1$-$C_4$-alkyl or $C_1$-$C_4$-haloalkyl having 1 to 5 halogen atoms, or A represents the radical of the formula (A 14)

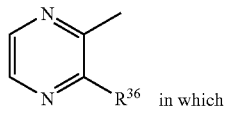
(A14)

in which $R^{36}$ represents hydrogen, halogen, $C_1$-$C_4$-alkyl or $C_1$-$C_4$-haloalkyl having 1 to 5 halogen atoms, or A represents the radical of the formula (A15)

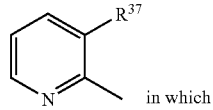
(A15)

in which $R^{37}$ represents halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms;

or

A represents the radical of the formula (A16)

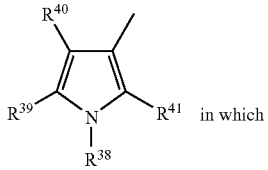
(A16)

in which $R^{38}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulphonyl, di($C_1$-$C_4$-alkyl)aminosulphonyl, $C_1$-$C_6$-alkylcarbonyl or in each case optionally substituted phenylsulphonyl or benzoyl, $R^{39}$ represents hydrogen, halogen, $C_1$-$C_4$-alkyl or $C_1$-$C_4$-haloalkyl having 1 to 5 halogen atoms, $R^{40}$ represents hydrogen, halogen, cyano, $C_1$-$C_4$-alkyl or $C_1$-$C_4$-haloalkyl having 1 to 5 halogen atoms, $R^{41}$ represents hydrogen, halogen, $C_1$-$C_4$-alkyl or $C_1$-$C_4$-haloalkyl having 1 to 5 halogen atoms, or A represents the radical of the formula (A17)

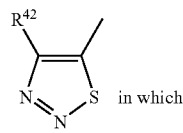
(A17)

in which $R^{42}$ represents $C_1$-$C_4$-alkyl.

The compounds according to the invention can, if appropriate, be present as mixtures of various possible isomeric forms, in particular of stereoisomers, such as, for example, E and Z, threo and erythro and also optical isomers, and, if appropriate, also of tautomers. What is claimed are both the E and the Z isomers, and also the threo and erythro and the optical isomers, any mixtures of these isomers and the possible tautomeric forms.

Furthermore, it has been found that hexylcarboxanilides of the formula (I) are obtained when a) carboxylic acid derivatives of the formula (II)

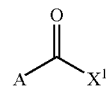
(II)

in which

A is as defined above and $X^1$ represents halogen or hydroxyl are reacted with an aniline derivative of the formula (III)

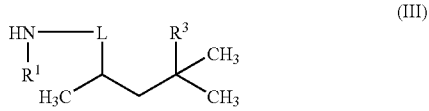

in which L, $R^1$ and $R^3$ are as defined above,
if appropriate in the presence of a catalyst, if appropriate in the presence of a condensing agent, if appropriate in the presence of an acid binder and if appropriate in the presence of a diluent, or b) hexylcarboxanilides of the formula (I-a)

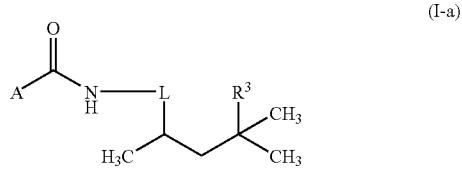

in which L, A and $R^3$ are as defined above
are reacted with halides of the formula (IV)

in which
$X^2$ represents chlorine, bromine or iodine,
$R^{1-A}$ represents $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-$C_1$-$C_3$-alkyl)carbonyl-$C_1$-$C_3$-alkyl, halo-$C_1$-$C_3$-alkoxy)carbonyl-$C_1$-$C_3$-alkyl having in each case 1 to 13 fluorine, chlorine and/or bromine atoms;
($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-Cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^4$, —CONR$^5$R$^6$ or —CH$_2$NR$^7$R$^8$, where $R^4$, $R^5$, $R^6$, $R^7$ and $R^8$ are as defined above
in the presence of a base and in the presence of a diluent.

Finally, it has been found that the novel hexylcarboxanilides of the formula (I) have very good microbicidal properties and can be used for controlling unwanted microorganisms both in crop protection and in the protection of materials.

The formula (I) provides a general definition of the hexylcarboxanilides according to the invention. Preferred radical definitions of the formulae shown above and below are given below. These definitions apply both to the end products of the formula (I) and likewise to all intermediates.

L preferably represents L-1 where $R^2$ may in each case have the general, preferred, particularly preferred, very particularly preferred or especially preferred meanings.
L furthermore preferably represents L-2.
L furthermore preferably represents L-3.
L furthermore preferably represents L-4.
L particularly preferably represents L-1, where $R^2$ may in each case have the general, preferred, particularly preferred, very particularly preferred or especially preferred meanings.
L furthermore particularly preferably represents L-2.
L very particularly represents L-1 where $R^2$ may in each case have the general, preferred, particularly preferred, very particularly preferred or especially preferred meanings.
$R^1$ preferably represents hydrogen, $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-Cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo($C_1$-$C_3$-alkoxy)carbonyl-$C_1$-$C_3$-alkyl having in each case 1 to 13 fluorine, chlorine and/or bromine atoms;
($C_1$-$C_6$-alkyl)carbonyl, ($C_1$-$C_4$-alkoxy)carbonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)$R^4$, —CONR$^5$R$^6$ or —CH$_2$NR$^7$R$^8$.
$R^1$ particularly preferably represents hydrogen, methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methylsulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —(CH$_2$)$_2$—CO—CH$_3$, —(CH$_2$)$_2$—CO—CH$_2$CH$_3$, —(CH$_2$)$_2$—CO—CH(CH$_3$)$_2$, —CH$_2$—CO$_2$CH$_3$, —CH$_2$—CO$_2$CH$_2$CH$_3$, —CH$_2$—CO$_2$CH(CH$_3$)$_2$, —(CH$_2$)$_2$—CO$_2$CH$_3$, —(CH$_2$)$_2$—CO$_2$CH$_2$CH$_3$, —(CH$_2$)$_2$—CO$_2$CH(CH$_3$)$_2$, —CH$_2$—CO$_2$—CF$_3$, —CH$_2$—CO—CCl$_3$, —CH$_2$—CO—CH$_2$CF$_3$, —CH$_2$—CO—CH$_2$CCl$_3$, —(CH$_2$)$_2$—CO—CH$_2$CF$_3$, —(CH$_2$)$_2$—CO—CH$_2$CCl$_3$, —CH$_2$—CO$_2$CH$_2$CF$_3$, —CH$_2$—CO$_2$CF$_2$CF$_3$, —CH$_2$—CO$_2$CH$_2$CCl$_3$, —CH$_2$—CO$_2$CCl$_2$CCl$_3$, —(CH$_2$)$_2$—CO$_2$CH$_2$CF$_3$, —(CH$_2$)$_2$CO$_2$CF$_2$CF$_3$, —(CH$_2$)$_2$—CO$_2$CH$_2$CCl$_3$, —(CH$_2$)$_2$—CO$_2$CCl$_2$CCl$_3$;
methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^5$, —CONR$^6$R$^7$ or —CH$_2$NR$^8$R$^9$.
$R^1$ very particularly preferably represents hydrogen, methyl, methoxymethyl, formyl, —CH$_2$—CHO, —(CH$_2$)$_2$—CHO, —CH$_2$—CO—CH$_3$, —CH$_2$—CO—CH$_2$CH$_3$, —CH$_2$—CO—CH(CH$_3$)$_2$, —C(=O)CHO, —C(=O)C (=O)CH$_3$, —C(=O)C(=O)CH$_2$OCH$_3$, —C(=O) CO$_2$CH$_3$, —C(=O)CO$_2$CH$_2$CH$_3$.

R$^2$ preferably represents hydrogen.

R$^2$ furthermore preferably represents fluorine, where fluorine is particularly preferably located in the 4-, 5- or 6-position, very particularly preferably in the 4- or 6-position, especially in the 4-position, of the anilide radical [cf. formula (I) above].

R$^2$ furthermore preferably represents chlorine, where chlorine is particularly preferably located in the 5-position of the anilide radical [cf. formula (I) above]. Chlorine is furthermore particularly preferably located in the 4-position of the anilide radical.

R$^2$ furthermore preferably represents methyl, where methyl is particularly preferably located in the 3-position of the anilide radical [cf. formula (I) above].

R$^2$ furthermore preferably represents trifluoromethyl, where trifluoromethyl is particularly preferably located in the 4- or 5-position of the anilide radical [cf. formula (I) above].

R$^3$ preferably represents fluorine, chlorine, bromine, iodine, C$_1$-C$_6$-alkyl, C$_1$-C$_6$-haloalkyl having in each case 1 to 13 fluorine, chlorine and/or bromine atoms.

R$^3$ particularly preferably represents fluorine, chlorine, bromine, methyl, ethyl, n-, isopropyl, n-, iso-, sec-, tert-butyl or C$_1$-C$_4$-haloalkyl having in each case 1 to 9 fluorine, chlorine and/or bromine atoms.

R$^3$ very particularly preferably represents fluorine, chlorine, methyl, ethyl or trifluoromethyl.

R$^4$ preferably represents hydrogen, C$_1$-C$_6$-alkyl, C$_1$-C$_4$-alkoxy, C$_1$-C$_3$-alkoxy-C$_1$-C$_3$-alkyl, C$_3$-C$_6$-cycloalkyl; C$_1$-C$_4$-haloalkyl, C$_1$-C$_4$-haloalkoxy, halo-C$_1$-C$_3$-alkoxy-C$_1$-C$_3$-alkyl, C$_3$-C$_6$-halocycloalkyl having in each case 1 to 9 fluorine, chlorine and/or bromine atoms.

R$^4$ particularly preferably represents hydrogen, methyl, ethyl, n- or isopropyl, tert-butyl, methoxy, ethoxy, n- or isopropoxy, tert-butoxy, methoxymethyl, cyclopropyl; trifluoromethyl, trifluoromethoxy.

R$^5$ and R$^6$ independently of one another preferably represent hydrogen, C$_1$-C$_6$-alkyl, C$_1$-C$_3$-alkoxy-C$_1$-C$_3$-alkyl, C$_3$-C$_6$-cycloalkyl; C$_1$-C$_4$-haloalkyl, halo-C$_1$-C$_3$-alkoxy-C$_1$-C$_3$-alkyl, C$_3$-C$_6$-halocycloalkyl having in each case 1 to 9 fluorine, chlorine and/or bromine atoms.

R$^5$ and R$^6$ furthermore together with the nitrogen atom to which they are attached preferably represent a saturated heterocycle having 5 or 6 ring atoms which is optionally mono- to tetrasubstituted by identical or different substituents from the group consisting of halogen and C$_1$-C$_4$-alkyl, where the heterocycle may contain 1 or 2 further non-adjacent heteroatoms from the group consisting of oxygen, sulphur and NR$^9$.

R$^5$ and R$^6$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

R$^5$ and R$^6$ furthermore together with the nitrogen atom to which they are attached particularly preferably represent a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by R$^9$.

R$^7$ and R$^8$ independently of one another preferably represent hydrogen, C$_1$-C$_6$-alkyl, C$_3$-C$_6$-cycloalkyl; C$_1$-C$_4$-haloalkyl, C$_3$-C$_6$-halocycloalkyl having in each case 1 to 9 fluorine, chlorine and/or bromine atoms.

R$^7$ and R$^8$ furthermore together with the nitrogen atom to which they are attached preferably represent a saturated heterocycle having 5 or 6 ring atoms which is optionally mono- or polysubstituted by identical or different substituents from the group consisting of halogen and C$_1$-C$_4$-alkyl, where the heterocycle may contain 1 or 2 further non-adjacent heteroatoms from the group consisting of oxygen, sulphur and NR$^9$.

R$^7$ and R$^8$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

R$^7$ and R$^8$ furthermore together with the nitrogen atom to which they are attached particularly preferably represent a saturated heterocycle from the group consisting of morpholine, thiomorpholine and piperazine which is optionally mono- to tetrasubstituted by identical or different substituents from the group consisting of fluorine, chlorine, bromine and methyl, where the piperazine may be substituted on the second nitrogen atom by R$^9$.

R$^9$ preferably represents hydrogen or C$_1$-C$_4$-alkyl.

R$^9$ particularly preferably represents hydrogen, methyl, ethyl, n- or isopropyl, n-, iso-, sec- or tert-butyl.

A particularly represents one of the radicals A1, A2, A3, A4, A5, A8, A9, A10, A11, A13, A15, A16 or A17 given above.

A particularly preferably represents one of the radicals A1, A2, A4, A5, A8, A10, A11, A13, A15, A16 or A17 given above.

A very particularly preferably represents the radical A1.

A furthermore very particularly preferably represents the radical A2.

A furthermore very particularly preferably represents the radical A4.

A furthermore very particularly preferably represents the radical A5.

A furthermore very particularly preferably represents the radical A8.

A furthermore very particularly preferably represents the radical A10.

A furthermore very particularly preferably represents the radical A11.

A furthermore very particularly preferably represents the radical A13.

A furthermore very particularly preferably represents the radical A15.

A furthermore very particularly preferably represents the radical A17.

R$^{10}$ preferably represents hydrogen, hydroxyl, formyl, cyano, fluorine, chlorine, bromine, methyl, ethyl, isopropyl, methoxy, ethoxy, methylthio, ethylthio, cyclopropyl, C$_1$-C$_2$-haloalkyl, C$_1$-C$_2$-haloalkoxy having in each case 1 to 5 fluorine, chlorine and/or bromine atoms, trifluoromethylthio, difluoromethylthio, aminocarbonyl, aminocarbonylmethyl or aminocarbonylethyl.

R$^{10}$ particularly preferably represents hydrogen, hydroxyl, formyl, fluorine, chlorine, bromine, methyl, ethyl, isopropyl methoxy, ethoxy, monofluoromethyl, monofluoroethyl, difluoromethyl, trifluoromethyl, difluorochloromethyl, trichloromethyl, dichloromethyl, pentafluoroethyl, cyclopropyl, methoxy, ethoxy, trifluoromethoxy, difluoromethoxy, trichloromethoxy, methylthio, ethylthio, trifluoromethylthio or difluoromethylthio.

$R^{10}$ very particularly preferably represents hydrogen, hydroxyl, formyl, fluorine, chlorine, bromine, methyl, ethyl, isopropyl, methoxy, cyclopropyl, monofluoromethyl, monofluoroethyl, difluoromethyl, dichloromethyl, trifluoromethyl, difluorochloromethyl, trichloromethyl, —CHFCH₃ or difluoromethoxy.

$R^{10}$ especially preferably represents hydrogen, hydroxyl, formyl, chlorine, methyl, ethyl, methoxy, cyclopropyl, monofluoromethyl, difluoromethyl, dichloromethyl, trifluoromethyl, —CHFCH₃ or difluoromethoxy.

$R^{11}$ preferably represents hydrogen, chlorine, bromine, iodine, methyl, ethyl, methoxy, ethoxy, methylthio, ethylthio, $C_1$-$C_2$-haloalkyl having 1 to 5 fluorine, chlorine and/or bromine atoms, $R^{11}$ particularly preferably represents hydrogen, chlorine, bromine, iodine, methyl or —CHFCH₃.

$R^{11}$ very particularly preferably represents hydrogen, chlorine, methyl or —CHFCH₃.

$R^{12}$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.

$R^{12}$ particularly preferably represents hydrogen, methyl, ethyl, isopropyl, trifluoromethyl, difluoromethyl, hydroxymethyl, hydroxyethyl or phenyl.

$R^{12}$ very particularly preferably represents hydrogen, methyl, trifluoromethyl or phenyl.

$R^{12}$ especially preferably represents methyl.

$R^{13}$ and $R^{14}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{13}$ and $R^{14}$ independently of one another particularly preferably represent hydrogen, fluorine, chlorine, bromine, methyl, ethyl, difluoromethyl, trifluoromethyl, difluorochloromethyl or trichloromethyl.

$R^{13}$ and $R^{14}$ independently of one another very particularly preferably represent hydrogen, fluorine, chlorine, bromine or methyl.

$R^{13}$ and $R^{14}$ especially preferably each represent hydrogen.

$R^{15}$ preferably represents fluorine, chlorine, bromine, iodine, cyano, methyl, ethyl, $C_1$-$C_2$-haloalkyl or $C_1$-$C_2$-haloalkoxy having in each case 1 to 5 fluorine, chlorine and/or bromine atoms.

$R^{15}$ particularly preferably represents fluorine, chlorine, bromine, iodine, cyano, methyl, trifluoromethyl, trifluoromethoxy, difluoromethoxy, difluorochloromethoxy or trichloromethoxy.

$R^{15}$ very particularly preferably represents fluorine, chlorine, bromine, iodine, methyl, trifluoromethyl or trifluoromethoxy.

$R^{15}$ especially preferably represents chlorine or methyl.

$R^{16}$ and $R^{17}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^{16}$ and $R^{17}$ independently of one another particularly preferably represent hydrogen, fluorine, chlorine, bromine, methyl, ethyl, difluoromethyl, trifluoromethyl, difluorochloromethyl or trichloromethyl.

$R^{16}$ and $R^{17}$ independently of one another very particularly preferably represent hydrogen, fluorine, chlorine, bromine or methyl.

$R^{16}$ and $R^{17}$ especially preferably each represent hydrogen.

$R^{18}$ preferably represents hydrogen, methyl, ethyl or $C_1$-$C_2$-haloalkyl having 1 to 5 fluorine, chlorine and/or bromine atoms.

$R^{18}$ particularly preferably represents hydrogen, methyl or trifluoromethyl.

$R^{18}$ very particularly preferably represents methyl.

$R^{19}$ preferably represents fluorine, chlorine, bromine, iodine, hydroxyl, cyano, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{19}$ particularly preferably represents fluorine, chlorine, bromine, iodine, hydroxyl, cyano, methyl, ethyl, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{19}$ very particularly preferably represents fluorine, chlorine, bromine, iodine, hydroxyl, methyl, trifluoromethyl, difluoromethyl or trichloromethyl.

$R^{20}$ preferably represents hydrogen, fluorine, chlorine, bromine, iodine, cyano, $C_1$-$C_4$-alkyl, methoxy, ethoxy, methylthio, ethylthio, $C_1$-$C_2$-haloalkyl or $C_1$-$C_2$-haloalkoxy having in each case 1 to 5 fluorine, chlorine and/or bromine atoms, $C_1$-$C_2$-alkylsulphinyl or $C_1$-$C_2$-alkylsulphonyl.

$R^{20}$ particularly preferably represents hydrogen, fluorine, chlorine, bromine, iodine, cyano, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methylsulphinyl or methylsulphonyl.

$R^{20}$ very particularly preferably represents hydrogen, fluorine, chlorine, bromine, iodine, n-propyl, isopropyl, n-butyl, isobutyl, sec-butyl, tert-butyl, trifluoromethyl, difluoromethyl, trichloromethyl, methylsulphinyl or methylsulphonyl.

$R^{20}$ especially preferably represents hydrogen or trifluoromethyl.

$R^{21}$ preferably represents methyl, ethyl or $C_1$-$C_2$-haloalkyl having 1 to 5 fluorine, chlorine and/or bromine atoms.

$R^{21}$ particularly preferably represents methyl, ethyl, trifluoromethyl, difluoromethyl, difluorochloromethyl or trichloromethyl.

$R^{21}$ very particularly preferably represents methyl, trifluoromethyl, difluoromethyl or trichloromethyl.

$R^{22}$ preferably represents methyl, ethyl trifluoromethyl, difluoromethyl, difluorochloromethyl or trichloromethyl.

$R^{22}$ particularly preferably represents methyl, trifluoromethyl, difluoromethyl or trichloromethyl.

$R^{23}$ and $R^{24}$ independently of one another preferably represent hydrogen, fluorine, chlorine, bromine, amino, methyl, ethyl or $C_1$-$C_2$-haloalkyl having 1 to 5 fluorine, chlorine and/or bromine atoms.

$R^{23}$ and $R^{24}$ independently of one another particularly preferably represent hydrogen, fluorine, chlorine, bromine, methyl, ethyl, trifluoromethyl, difluoromethyl, difluorochloromethyl or trichloromethyl.

$R^{23}$ and $R^{24}$ independently of one another very particularly preferably represent hydrogen, fluorine, chlorine, bromine or methyl.

$R^{23}$ and $R^{24}$ especially preferably each represent hydrogen.

$R^{25}$ preferably represents hydrogen, methyl, ethyl or $C_1$-$C_2$-haloalkyl having 1 to 5 fluorine, chlorine and/or bromine atoms.

$R^{25}$ particularly preferably represents hydrogen, methyl, ethyl, trifluoromethyl, difluoromethyl, difluorochloromethyl or trichloromethyl.

$R^{25}$ very particularly preferably represents hydrogen, methyl, trifluoromethyl, difluoromethyl or trichloromethyl.

$R^{25}$ especially preferably represents methyl or trifluoromethyl.

$R^{26}$ and $R^{27}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine atoms.

$R^{26}$ and $R^{27}$ independently of one another particularly preferably represent hydrogen, fluorine, chlorine, bromine, nitro, methyl, ethyl, trifluoromethyl, difluoromethyl, difluorochloromethyl or trichloromethyl.

$R^{26}$ and $R^{27}$ independently of one another very particularly preferably represent hydrogen, fluorine, chlorine, bromine or methyl.

$R^{26}$ and $R^{27}$ especially preferably each represent hydrogen.

$R^{28}$ preferably represents fluorine, chlorine, bromine, methyl, ethyl or $C_1$-$C_2$-haloalkyl having 1 to 5 fluorine, chlorine and/or bromine atoms.

$R^{28}$ particularly preferably represents fluorine, chlorine, bromine, methyl, ethyl, trifluoromethyl, difluoromethyl, difluorochloromethyl or trichloromethyl.

$R^{28}$ very particularly preferably represents fluorine, chlorine, bromine, methyl, trifluoromethyl, difluoromethyl or trichloromethyl.

$R^{28}$ especially preferably represents methyl.

$R^{29}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{29}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{29}$ very particularly preferably represents hydrogen, fluorine, chlorine, bromine, amino, methylamino, dimethylamino, methyl, trifluoromethyl, difluoromethyl or trichloromethyl.

$R^{29}$ especially preferably represents hydrogen, chlorine, amino, methylamino, dimethylamino, methyl or trifluoromethyl.

$R^{30}$ preferably represents fluorine, chlorine, bromine, hydroxyl, methyl, ethyl, methoxy, ethoxy, cyclopropyl, $C_1$-$C_2$-haloalkyl or $C_1$-$C_2$-haloalkoxy having 1 to 5 fluorine, chlorine and/or bromine atoms.

$R^{30}$ particularly preferably represents fluorine, chlorine, bromine, hydroxyl, methyl, ethyl, methoxy, ethoxy, cyclopropyl, trifluoromethyl, difluoromethyl, difluorochloromethyl or trichloromethyl.

$R^{30}$ very particularly preferably represents, fluorine, chlorine, bromine, hydroxyl, methyl, methoxy, cyclopropyl, trifluoromethyl, difluoromethyl or trichloromethyl.

$R^{31}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{31}$ particularly preferably represents hydrogen, fluorine, chlorine, bromine, amino, methylamino, dimethylamino, cyano, methyl, ethyl, trifluoromethyl, difluoromethyl, difluorochloromethyl or trichloromethyl.

$R^{31}$ very particularly preferably represents hydrogen, fluorine, chlorine, bromine, amino, methylamino, dimethylamino, methyl, trifluoromethyl, difluoromethyl or trichloromethyl.

$R^3$ especially preferably represents amino, methylamino, dimethylamino, methyl or trifluoromethyl.

$R^{32}$ preferably represents fluorine, chlorine, bromine, methyl, ethyl or $C_1$-$C_2$-haloalkyl having 1 to 5 fluorine, chlorine and/or bromine atoms.

$R^{32}$ particularly preferably represents fluorine, chlorine, bromine, methyl, ethyl, trifluoromethyl, difluoromethyl, difluorochloromethyl or trichloromethyl.

$R^{32}$ very particularly preferably represents fluorine, chlorine, bromine, methyl, trifluoromethyl, difluoromethyl or trichloromethyl.

$R^{32}$ especially preferably represents methyl, trifluoromethyl or difluoromethyl.

$R^{33}$ preferably represents hydrogen, methyl or ethyl.

$R^{33}$ particularly preferably represents methyl.

$R^{34}$ preferably represents fluorine, chlorine, bromine, methyl or ethyl.

$R^{34}$ particularly preferably represents fluorine, chlorine or methyl.

$R^{35}$ preferably represents methyl, ethyl or $C_1$-$C_2$-haloalkyl having 1 to 5 fluorine, chlorine and/or bromine atoms.

$R^{35}$ particularly preferably represents methyl, ethyl, trifluoromethyl, difluoromethyl, difluorochloromethyl or trichloromethyl.

$R^{35}$ very particularly preferably represents methyl, trifluoromethyl, difluoromethyl or trichloromethyl.

$R^{35}$ especially preferably represents methyl or trifluoromethyl.

$R^{36}$ preferably represents hydrogen, fluorine, chlorine, bromine, methyl, ethyl or $C_1$-$C_2$-haloalkyl having 1 to 5 fluorine, chlorine and/or bromine atoms.

$R^{36}$ particularly preferably represents hydrogen, fluorine, chlorine, bromine, methyl or trifluoromethyl.

$R^{36}$ very particularly preferably represents hydrogen or chlorine.

$R^{37}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{37}$ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl, trichloromethyl.

$R^{37}$ very particularly preferably represents fluorine, chlorine, bromine, iodine, methyl, trifluoromethyl, difluoromethyl or trichloromethyl.

$R^{38}$ preferably represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulphonyl or dimethylaminosulphonyl.

$R^{38}$ particularly preferably represents hydrogen, methyl, ethyl, trifluoromethyl, methoxymethyl, ethoxymethyl, hydroxymethyl or hydroxyethyl.

$R^{38}$ very particularly preferably represents methyl or methoxymethyl.

$R^{39}$ preferably represents hydrogen, fluorine, chlorine, bromine, methyl, ethyl or $C_1$-$C_2$-haloalkyl having 1 to 5 fluorine, chlorine and/or bromine atoms.

$R^{39}$ particularly preferably represents hydrogen, fluorine, chlorine, bromine, methyl, ethyl, trifluoromethyl, difluoromethyl or trichloromethyl.

$R^{39}$ very particularly preferably represents hydrogen or methyl.

$R^{40}$ preferably represents hydrogen, fluorine, chlorine, bromine, cyano, methyl, ethyl, isopropyl or $C_1$-$C_2$-haloalkyl having 1 to 5 fluorine, chlorine and/or bromine atoms.

$R^{40}$ particularly preferably represents hydrogen, fluorine, chlorine, bromine, cyano, methyl, ethyl, isopropyl, trifluoromethyl, difluoromethyl, difluorochloromethyl or trichloromethyl.

$R^{40}$ very particularly preferably represents hydrogen, fluorine, methyl or trifluoromethyl.

$R^{41}$ preferably represents hydrogen, fluorine, chlorine, bromine, methyl, ethyl or $C_1$-$C_2$-haloalkyl having 1 to 5 fluorine; chlorine and/or bromine atoms.

$R^{41}$ particularly preferably represents hydrogen, fluorine, chlorine, bromine, iodine, methyl or trifluoromethyl.

$R^{41}$ very particularly preferably represents hydrogen or trifluoromethyl.

$R^{42}$ preferably represents methyl, ethyl, n-propyl or isopropyl.

$R^{42}$ particularly preferably represents methyl or ethyl.

Emphasis is given to compounds of the formula (I) in which L represents L-1, where $R^2$ has the general meanings given above.

Emphasis is given to compounds of the formula (I) in which L represents L-1, where $R^2$ has the preferred meanings given above.

Emphasis is given to compounds of the formula (I) in which L represents L-1, where $R^2$ has the particularly preferred meanings given above.

Emphasis is given to compounds of the formula (I) in which L represents L-1, where $R^2$ has the very particularly preferred meanings given above.

Emphasis is given to compounds of the formula (I) in which L represents L-1, where $R^2$ has the especially preferred meanings given above.

Emphasis is given to compounds of the formula (I) in which L represents L-2.

Emphasis is given to compounds of the formula (I) in which $R^1$ represents hydrogen.

Emphasis is given to compounds of the formula (I) in which $R^1$ represents formyl.

Emphasis is furthermore given to compounds of the formula (I) in which $R^1$ represents —C(=O)C(=O)$R^4$ where $R^4$ is as defined above.

Emphasis is given to compounds of the formula (I) in which A represents A1.

Saturated or unsaturated hydrocarbon radicals, such as alkyl or alkenyl, can in each case be straight-chain or branched, as far as this is possible, including in combination with heteroatoms, such as, for example, in alkoxy.

Optionally substituted radicals can be mono- or polysubstituted, where in the case of polysubstitution the substituents can be identical or different.

Halogen-substituted radicals, such as, for example, haloalkyl, are mono- or polyhalogenated. In the case of polyhalogenation, the halogen atoms can be identical or different. Here, halogen represents fluorine, chlorine, bromine and iodine, in particular fluorine, chlorine and bromine.

However, the general or preferred radical definitions or illustrations given above can also be combined with one another as desired, i.e. between the respective ranges and preferred ranges. The definitions apply both to the end products and, correspondingly, to the precursors and intermediates.

The definitions mentioned can be combined with one another as desired. Moreover, individual definitions may not apply.

Preference, particular preference or very particular preference is given to the compounds of the formula (I) which carry the substituents mentioned as being preferred, particularly preferred and very particularly preferred, respectively.

Description of the Processes According to the Invention for Preparing the Hexylcarboxanilides of the Formula (I) and the Intermediates Process (a)

Using 3-dichloromethyl-1-methyl-1H-pyrazole-4-carbonyl chloride and [2-(1,3,3-trimethylbutyl)-phenyl]amine as starting materials, the process (a) according to the invention can be illustrated by the formula scheme below:

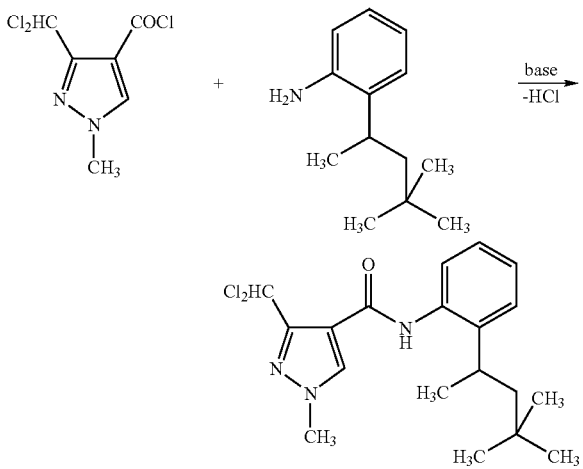

Formula (II) provides a general definition of the carboxylic acid derivatives required as starting materials for carrying out the process (a) according to the invention. In this formula (II), A preferably, particularly pin connection with the description of the compounds of the formula (I) according to the invention as being preferred, particularly preferred and very particularly preferred, respectively, for A. $X^1$ preferably represents chlorine, bromine or hydroxyl.

Most of the carboxylic acid derivatives of the formula (II) are known and/or can be prepared by known processes (cf. WO 93/11117, EP-A 0 545 099, EP-A 0 589 301 and EP-A 0 589 313).

3-Dichloromethyl-1H-pyrazole-4-carboxylic acid derivatives of the formula (II-a)

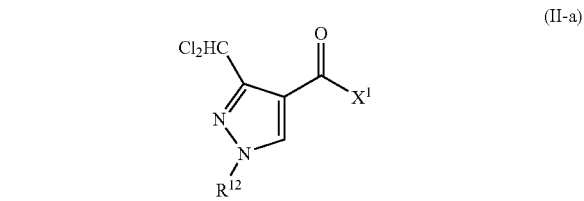

(II-a)

in which $R^{12}$ is as defined above, $X^1$ represents halogen or hydroxyl can be obtained when, in a first step, ketoacetals of the formula (V)

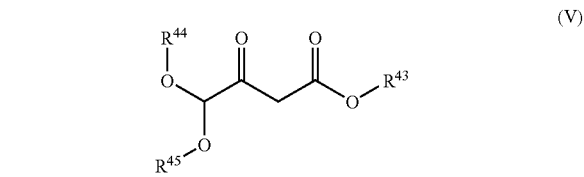

(V)

in which $R^{43}$ represents $C_1$-$C_4$-alkyl, preferably methyl, ethyl, n-, isopropyl, n-, sec-, tert-butyl, $R^{44}$ and $R^{45}$ each represent methyl or ethyl, or $R^{44}$ and $R^{45}$ together represent —(CH$_2$)$_3$— or —CH$_2$—C(CH$_3$)$_2$—CH$_2$— are reacted with alkyl orthoformates of the formula (VI)

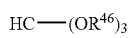
(VI)

in which $R^{46}$ represents $C_1$-$C_4$-alkyl, preferably methyl, ethyl, n-, isopropyl, n-, sec-, tert-butyl in the presence of an anhydride (for example acetic anhydride)

and the resulting compounds of the formula (VII)

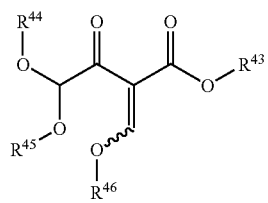
(VII)

in which $R^{43}$, $R^{44}$, $R^{45}$ and $R^{46}$ are as defined above, are in a second step, reacted with hydrazine derivatives of the formula (VIII)

(VIII)

in which $R^{12}$ is as defined above in the presence of a diluent (for example methanol)

and the resulting pyrazole derivatives of the formula (IX)

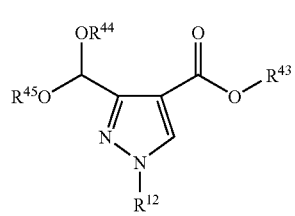
(IX)

in which $R^{12}$, $R^{43}$, $R^{44}$ and $R^{45}$ are as defined above are, in a third step, reacted in the presence of an acid (for example hydrochloric acid) and in the presence of a diluent (for example dioxane)

and the resulting 3-formyl-1H-pyrazole-4-carboxylic esters of the formula (X)

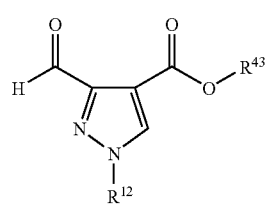
(X)

in which $R^{12}$ and $R^{43}$ are as defined above are either a) in a fourth step hydrolyzed in the presence of a base (for example lithium hydroxide) and in the presence of a diluent (for example tetrahydrofuran)

and the resulting 3-formyl-1H-pyrazole-4-carboxylic acids of the formula (XI)

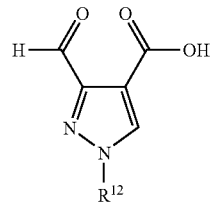
(XI)

in which $R^{12}$ is as defined above are then reacted with a chlorinating agent (for example phosphorus pentachloride) in the presence of a diluent (for example dichloromethane), or b) in a fourth step reacted with a chlorinating agent (for example phosphorus pentachloride) in the presence of a diluent (for example dichloromethane)

and the resulting 3-dichloromethyl-1H-pyrazole-4-carboxylic esters of the formula (XII)

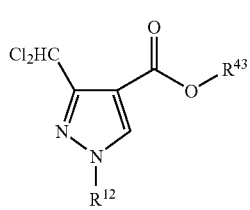
(XII)

in which $R^{12}$ and $R^{43}$ are as defined above are then hydrolyzed in the presence of a base (for example lithium hydroxide) and in the presence of a diluent (for example tetrahydrofuran).

The formula (III) provides a general definition of the aniline derivatives furthermore required as starting materials for carrying out the process (a) according to the invention. In this formula (III), L, $R^1$ and $R^3$ preferably, particularly preferably and very particularly preferably have those meanings which have already been mentioned in connection with the description of the compounds of the formula (I) according to the invention as being preferred, particularly preferred and very particularly preferred for these radicals.

Some of the aniline derivatives of the formula (III) in which L represents L-1 are novel. Aniline derivatives of formula (III) in which L represents L-1 can be prepared by c) reacting, in a first step, an aniline derivative of the formula (XIII)

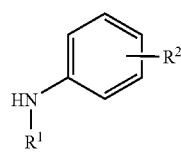
(XIII)

in which $R^1$ and $R^2$ are as defined above with an alkene of the formula (XIV)

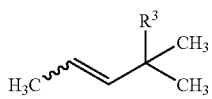

(XIV)

in which $R^3$ is as defined above
in the presence of a catalyst, if appropriate in the presence of a base and if appropriate in the presence of a diluent, and hydrogenating the resulting alkene aniline of the formula (XV)

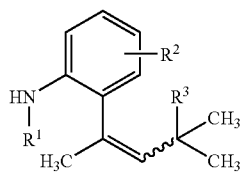

(XV)

in which $R^1$, $R^2$ and $R^3$ are as defined above
in a second step, if appropriate in the presence of a diluent and if appropriate in the presence of a catalyst.

The formula (XIII) provides a general definition of the aniline derivatives required as starting materials for carrying out the process (c) according to the invention. In this formula (XIII), $R^1$ and $R^2$ preferably, particularly preferably and very particularly preferably have those meanings which have already been mentioned in connection with the description of the compounds of the formula (I) according to the invention as being preferred, particularly preferred and very particularly preferred for these radicals.

Aniline derivatives of the formula (XIII) are known or can be obtained by known methods. Aniline derivatives of the formula (XIII) in which $R^1$ does not represent hydrogen can be obtained by reacting anilines of the formula (XIII-a)

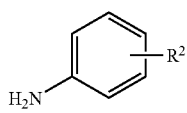

(XIII-a)

in which $R^2$ is as defined above
with halides of the formula (IV)

$R^{1-A}-X^2$  (IV)

in which $R^{1-A}$ and $X^2$ are as defined above in the presence of a base and in the presence of a diluent. [The reaction conditions of process (b) apply correspondingly.]

The formula (XIV) provides a general definition of the alkenes furthermore required as starting materials for carrying out the process (c) according to the invention. In this formula (XIV), $R^3$ preferably, particularly preferably and very particularly preferably has those meanings which have already been mentioned in connection with the description of the compounds of the formula (I) according to the invention as being preferred, particularly preferred and very particularly preferred for this radical.

Alkenes of the formula (XIV) are known or can be obtained by known methods.

The formula (XV) provides a general definition of the alkene anilines which are intermediates obtained when carrying out the process (c) according to the invention. In this formula (XV), $R^1$, $R^2$ and $R^3$ preferably, particularly preferably and very particularly preferably have those meanings which have already been mentioned in connection with the description of the compounds of the formula (I) according to the invention as being preferred, particularly preferred and very particularly preferred for these radicals.

Some of the alkene anilines of the formula (XV) are known.

The process (c) according to the invention can be carried out in various variants. Thus, it is possible to initially react anilines of the formula (XIII-a) with alkenes of the formula (XIV) to give the corresponding aniline derivatives of the formula (III-a)

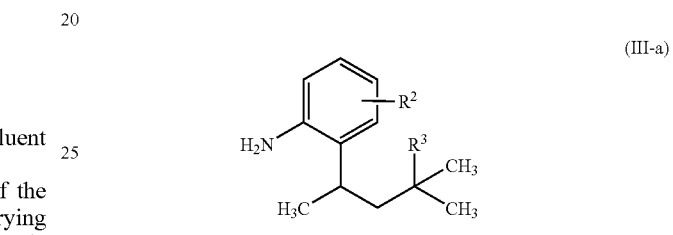

(III-a)

in which $R^2$ and $R^3$ are as defined above, which are then, if appropriate, reacted with halides of the formula (IV)

$R^{1-A}-X^2$  (IV)

in which $R^{1-A}$ and $X^2$ are as defined above in the presence of a base and in the presence of a diluent to give the corresponding aniline derivatives of the formula (III). [The reaction conditions of process (b) apply correspondingly.]

However, it is also possible to carry out the reaction with a halide of the formula (IV) at the stage of the alkene anilines of the formula (XV) and to hydrogenate afterwards.

Aniline derivatives of the formula (III-b)

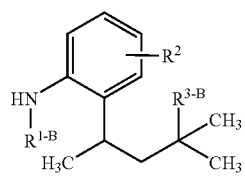

(III-b)

in which
a) $R^{1-B}$ represents hydrogen and
$R^{3-B}$ represents halogen, $C_3$-$C_8$-alkyl, $C_1$-$C_8$-haloalkyl,
or
b) $R^{1-B}$ represents $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$- haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)R$^4$, —CONR$^5$R$^6$ or —CH$_2$NR$^7$R$^8$, and R$^{3-B}$ represents hydrogen, halogen, $C_1$-$C_8$-alkyl, $C_1$-$C_8$-haloalkyl, and
R$^2$, R$^4$, R$^5$, R$^6$, R$^7$ and R$^8$ are each as defined above are novel and also form part of the subject-matter of this application.

The preferred, particularly preferred and very particularly preferred meanings of R$^1$ and R$^3$ apply correspondingly to R$^{1-B}$ and R$^{3-B}$, where in case a) R$^{1-B}$ always represents hydrogen and R$^{3-B}$ does not represent hydrogen, methyl or ethyl and in case b) R$^{1-B}$ does not represent hydrogen. The preferred, particularly preferred and very particularly preferred meanings of R$^2$, R$^4$, R$^5$, R$^6$, R$^7$ and R$^8$ also apply to the novel compounds of the formula (III-b).

Emphasis is given to compounds of the formula (III-b) in which R$^1$ and R$^2$ each represent hydrogen and R$^3$ represents fluorine, chlorine, methyl, ethyl, trifluoromethyl or pentafluoroethyl.

The aniline derivatives of the formula (III) in which L represents L-2, L-3 or L-4 are known and/or can be obtained by known processes (cf., for example, EP-A 1 036 793 and EP-A 0 737 682).

Aniline derivatives of the formula (III) in which L represents L-2, L-3 or LA and R$^1$ does not represent hydrogen can be obtained by reacting anilines of the formula (III-c)

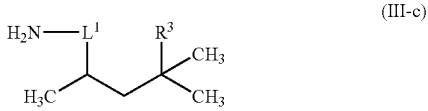

(III-c)

in which
L$^1$ represents L-2, L-3 or L-4 and
L-2, L-3, L-4 and R$^3$ are as defined above with halides of the formula (IV)

(IV)

in which R$_{1-A}$ and X$^2$ are as defined above in the presence of a base and in the presence of a diluent. [The reaction conditions of process (b) apply correspondingly.]

Process (b)
Using 1,3,5-trimethyl-N-[2-(1,3,3-trimethylbutyl)phenyl]-1H-pyrazole-4-carboxamide and ethyl chloro(oxo)acetate as starting materials, the course of the process (b) according to the invention can be illustrated by the formula scheme below:

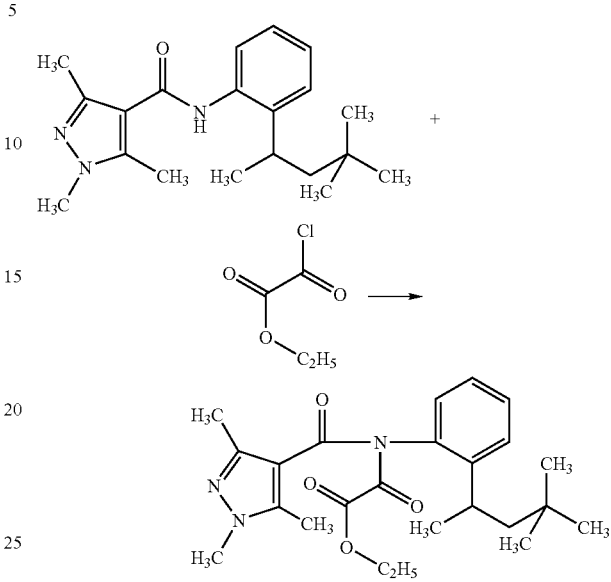

The formula (I-a) provides a general definition of the hexylcarboxanilides required as starting materials for carrying out the process (b) according to the invention. In this formula (I-a), R$^2$, R$^3$ and A preferably, particularly preferably and very particularly preferably have those meanings which have already been mentioned in connection with the description of the compounds of the formula (I) according to the invention as being preferred, particularly preferred and very particularly preferred, respectively, for these radicals.

The hexylcarboxanilides of the formula (I-a) are also compounds according to the invention and form part of the subject-matter of this application. They can be obtained by process (a) according to the invention (where R$^1$=hydrogen).

The formula (IV) provides a general definition of the halides furthermore required for carrying out the process (b) according to the invention.

R$^{1-A}$ preferably represents $C_1$-$C_6$-alkyl, $C_1$-$C_4$-alkylsulphinyl, $C_1$-$C_4$-alkylsulphonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulphinyl, $C_1$-$C_4$-haloalkylsulphonyl, halo-$C_1$-$C_3$-alkoxy-$C_1$-$C_3$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms;

($C_1$-$C_6$-alkyl)carbonyl, ($C_1$-$C_4$-alkoxy)cabonyl, ($C_1$-$C_3$-alkoxy-$C_1$-$C_3$-alkyl)carbonyl, ($C_3$-$C_6$-cycloalkyl)carbonyl; ($C_1$-$C_4$-haloalkyl)carbonyl, ($C_1$-$C_4$-haloalkoxy)carbonyl, (halo-$C_1$-$C_3$-alkoxy-$C_1$-$C_3$-alkyl)carbonyl, ($C_3$-$C_6$-halocycloalkyl)carbonyl having in each case 1 to 9 fluorine, chlorine and/or bromine atoms; or —C(=O)C(=O)R$^4$, —CONR$^5$R$^6$ or —CH$_2$NR$^7$R$^8$.

R$^{1-A}$ particularly preferably represents methyl, ethyl, n- or isopropyl, n-, iso-, sec- or tert-butyl, pentyl or hexyl, methylsulphinyl, ethylsulphinyl, n- or isopropylsulphinyl, n-, iso-, sec- or tert-butylsulphinyl, methyl sulphonyl, ethylsulphonyl, n- or isopropylsulphonyl, n-, iso-, sec- or tert-butylsulphonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulphinyl, trifluoromethylsulphonyl, trifluoromethoxymethyl; formyl, —$CH_2$—CHO, —$(CH_2)_2$—CHO, —$CH_2$—CO—$CH_3$, —$CH_2$—CO—$CH_2CH_3$, —$CH_2$—CO—$CH(CH_3)_2$, —$(CH_2)_2$—CO—$CH_3$, —$(CH_2)_2$—CO—$CH_2CH_3$, —$(CH_2)_2$—CO—$CH(CH_3)_2$, —$CH_2$—$CO_2CH_3$, —$CH_2$—$CO_2CH_2CH_3$, —$CH_2$—$CO_2CH(CH_3)_2$, —$(CH_2)_2$—$CO_2CH_3$, —$(CH_2)_2$—$CO_2CH_2CH_3$, —$(CH_2)_2$—$CO_2CH(CH_3)_2$, —$CH_2$—CO—$CF_3$, —$CH_2$—CO—$CCl_3$, —$CH_2$—CO—$CH_2CF_3$, —$CH_2$—CO—$CH_2CCl_3$, —$(CH_2)_2$—CO—$CH_2CF_3$, —$(CH_2)_2$—CO—$CH_2CCl_3$, —$CH_2$—$CO_2CH_2CF_3$, —$CH_2$—$CO_2CF_2CF_3$, —$CH_2$—$CO_2CH_2CCl_3$, —$CH_2$—$CO_2CCl_2CCl_3$, —$(CH_2)_2$—$CO_2CH_2CF_3$, —$(CH_2)_2$—$CO_2CF_2CF_3$, —$(CH_2)_2$—$CO_2CH_2CCl_3$, —$(CH_2)_2$—$CO_2CCl_2CCl_3$;

methylcarbonyl, ethylcarbonyl, n-propylcarbonyl, isopropylcarbonyl, tert-butylcarbonyl, methoxycarbonyl, ethoxycarbonyl, tert-butoxycarbonyl, cyclopropylcarbonyl; trifluoromethylcarbonyl, trifluoromethoxycarbonyl, or —C(=O)C(=O)$R^5$, —CON$R^6R^7$ or —$CH_2$N$R^8R^9$.

$R^{1-4}$ very particularly preferably represents methyl, methoxymethyl, formyl, —$CH_2$—CHO, —$(CH_2)_2$—CHO, —$CH_2$—CO—$CH_3$, —$CH_2$—CO—$CH_2CH_3$, —$CH_2$—CO—$CH(CH_3)_2$, —C(=O)CHO, —C(=O)C(=O)$CH_3$, —C(=O)C(=O)$CH_2OCH_3$, —C(=O)$CO_2CH_3$, —C(=O)$CO_2CH_2CH_3$.

$X^2$ preferably represents chlorine or bromine.

Halides of the formula (IV) are known.

Reaction Conditions

Suitable diluents for carrying out the process (a) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide.

The process (a) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The process (a) according to the invention is, if appropriate, carried out in the presence of a suitable condensing agent. Suitable condensing agents are all condensing agents customarily used for such amidation reactions. Acid halide formers, such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulphonyl chloride; carbodiimides, such as N,N'-dicyclohexylcarbodiimide (DCC), or other customary condensing agents, such as phosphorus pentoxide, polyphosphoric acid, N,N'-carbonyldiimidazole, 2-ethoxy-N-ethoxycarbonyl-1,2-dihydroquinoline (EEDQ), triphenylphosphine/carbon tetrachloride or bromotripyrrolidinophosphonium hexafluorophosphate may be mentioned by way of example.

The process (a) is, if appropriate, carried out in the presence of a catalyst. Examples which may be mentioned are 4-dimethylaminopyridine, 1-hydroxybenzotriazole or dimethylformamide.

When carrying out the process (a) according to the invention, the reaction temperatures can be varied within a relatively wide range. In general, the process is carried out at temperatures of from 0° C. to 150° C., preferably at temperatures of from 0° C. to 80° C.

For carrying out process (a) according to the invention for preparing the compounds of the formula (I), in general from 0.2 to 5 mol, preferably from 0.5 to 2 mol, of aniline derivative of the formula (III) are employed per mole of the carboxylic acid derivative of the formula (II).

Suitable diluents for carrying out the process (b) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole, or amides, such as N,N-dimethylformamide, N,N-dimethylacetamide, N-methylformanilide, N-methylpyrrolidone or hexamethylphosphoric triamide.

The process (b) according to the invention is carried out in the presence of a base. Suitable bases are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or caesium carbonate, and also tertiary amines, such as triethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process (b) according to the invention, the reaction temperatures can be varied within a relatively wide range. In general, the process is carried out at temperatures of from 0° C. to 150° C., preferably at temperatures of from 20° C. to 110° C.

For carrying out the process (b) according to the invention for preparing the compounds of the formula (I), in general from 0.2 to 5 mol, preferably from 0.5 to 2 mol, of halide of the formula (IV) are employed per mole of the hexylcarboxanilide of the formula (I-a).

Suitable diluents for carrying out the first step of the process (c) according to the invention are all inert organic solvents. These preferably include nitriles, such as acetonitrile, propionitrile, n- or i-butyronitrile or benzonitrile, or amides, such as N,N-dimethylformamide, N,N-dimethylacetamide, N-methylformanilide, N-methylpyrrolidone or hexamethylphosphoric triamide.

The first step of the process (c) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

The first step of the process (c) according to the invention is carried out in the presence of one or more catalysts.

These are in particular palladium salts or complexes. Preferred for this purpose are palladium chloride, palladium acetate, tetrakis(triphenylphosphine)palladium or bis(triphenylphosphine)-palladium dichloride. It is also possible to generate a palladium complex in the reaction mixture by adding a palladium salt and a complex ligand separately to the reaction.

Preferred ligands are organophosphorus compounds. Examples which may be mentioned are: triphenylphosphine, tri-o-tolylphosphine, 2,2'-bis(diphenylphosphino)-1,1'-binaphthyl, dicyclo-hexylphosphinebiphenyl, 1,4-bis(diphenylphosphino)butane, bisdiphenylphosphinoferrocene, di-tert-butylphosphino)biphenyl, di(cyclohexylphosphino) biphenyl, 2-dicyclohexylphosphino-2'-N,N-dimethylaminobiphenyl, tricyclohexylphosphine, tri-tert-butylphosphine. However, it is also possible to dispense with ligands.

The first step of the process (c) according to the invention is furthermore, if appropriate, carried out in the presence of a further metal salt, such as copper salts, for example copper(I) iodide.

When carrying out the first step of the process (c) according to the invention, the reaction temperatures can be varied within a relatively wide range. In general, the reaction is carried out at temperatures of from 20° C. to 180° C., preferably at temperatures of from 50° C. to 150° C.

For carrying out the first step of the process (c) according to the invention for preparing the alkene anilines of the formula (XV), in general from 1 to 5 mol, preferably from 1 to 3 mol, of alkene of the formula (XIV) are employed per mole of the aniline derivative of the formula (XIII).

Suitable diluents for carrying out the second step (hydrogenation) of the process (c) according to the invention are all inert organic solvents. These preferably include aliphatic or alicyclic hydrocarbons, such as, for example, petroleum ether, hexane, heptane, cyclohexane, methylcyclohexane or decalin; ethers, such as diethyl ether, diisopropyl ether, methyl tert-butyl ether, methyl tert-amyl ether, dioxane, tetrahydrofuran, 1,2-dimethoxyethane or 1,2-diethoxyethane; alcohols, such as methanol, ethanol, n- or isopropanol, n-, iso-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

The second step (hydrogenation) of the process (c) according to the invention is carried out in the presence of a catalyst. Suitable catalysts are all catalysts which are customarily used for hydrogenations. Examples which may be mentioned are: Raney nickel, palladium or platinum, if appropriate on a support, such as, for example activated carbon.

Instead of in the presence of hydrogen in combination with a catalyst, the hydrogenation in the second step of the process (c) according to the invention can also be carried out in the presence of triethylsilane.

When carrying out the second step of the process (c) according to the invention, the reaction temperatures can be varied within a relatively wide range. In general, the reaction is carried out at temperatures of from 0° C. to 150° C., preferably at temperatures of from 20° C. to 100° C.

The second step of the process (c) according to the invention is carried out under a hydrogen pressure between 0.5 and 200 bar, preferably between 2 and 50 bar, particularly preferably between 3 and 10 bar.

Unless indicated otherwise, all processes according to the invention are generally carried out under atmospheric pressure. However, it is also possible to operate under elevated or reduced pressure—in general between 0.1 bar and 10 bar.

The substances according to the invention have potent microbial activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha*;

*Venturia* species, such as, for example, *Venturia inaequalis*;

*Pyrenophora* species, such as, for example, *Pyrenophora teres* or *P. graminea* (conidia form: *Drechslera*; syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus*;

*Puccinia* species, such as, for example, *Puccinia recondita*;

*Sclerotinia* species, such as, for example, *Sclerotinia sclerotiorum*;

*Tilletia* species, such as, for example, *Tilletia caries*;

*Ustilago* species, such as, for example, *Ustilago nuda* or *Ustilago avenae*;

*Pellicularia* species, such as, for example, *Pellicularia sasakii*;

*Pyricularia* species, such as, for example, *Pyricularia oryzae*;

*Fusarium* species, such as, for example, *Fusarium culmorum*;

*Botrytis* species, such as, for example, *Botrytis cinerea*;

*Septoria* species, such as, for example, *Septoria nodorum*;

*Leptosphaeria* species, such as, for example, *Leptosphaeria nodorum*;

*Cercospora* species, such as, for example, *Cercospora canescens*;

*Alternaria* species, such as, for example, *Alternaria brassicae*; and

*Pseudocercosporella* species, such as, for example, *Pseudocercosporella herpotrichoides*,

*Rhizoctonia* species, such as, for example, *Rhizoctonia solani*.

The active compounds according to the invention also show a strong invigorating action in plants. Accordingly, they are suitable for mobilizing the internal defences of the plant against attack by unwanted microorganisms.

In the present context, plant-invigorating (resistance-inducing) compounds are to be understood as meaning substances which are capable of stimulating the defence system of plants such that, when the treated plants are subsequently inoculated with unwanted microorganisms, they display substantial resistance to these microorganisms.

In the present case, unwanted microorganisms are to be understood as meaning phytopathogenic fungi, bacteria and viruses. The compounds according to the invention can thus be used to protect plants within a certain period of time after treatment against attack by the pathogens mentioned.

The period of time for which this protection is achieved generally extends for 1 to 10 days, preferably 1 to 7 days, from the treatment of the plants with the active compounds.

The fact that the active compounds are well tolerated by plants at the concentrations required for controlling plant diseases permits the treatment of above-ground parts of plants, of propagation stock and seeds, and of the soil.

Here, the active compounds according to the invention can be used with particularly good results for controlling cereal diseases, such as, for example, against *Puccinia* species, and of diseases in viticulture and in the cultivation of fruits and vegetables, such as, for example, against *botrytis*, *Venturia* or *Alternaria* species.

The active compounds according to the invention are also suitable for increasing the yield of crops. In addition, they show reduced toxicity and are well tolerated by plants.

If appropriate, the active compounds according to the invention can, at certain concentrations and application rates, also be employed as herbicides, for regulating plant growth and for controlling animal pests. If appropriate, they can also be used as intermediates or precursors in the synthesis of other active compounds.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be tackifiers, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably tackifiers, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (*Basidiomycetes*) and against slime organisms and algae.

Microorganisms of the following genera may be mentioned as examples:

*Alternaria*, such as *Alternaria tenuis*,

*Aspergillus*, such as *Aspergillus niger*,

*Chaetomium*, such as *Chaetomium globosum*,

*Coniophora*, such as *Coniophora puetana*,

*Lentinus*, such as *Lentinus tigrinus*,

*Penicillium*, such as *Penicillium glaucum*,

*Polyporus*, such as *Polyporus versicolor*,

*Aureobasidium*, such as *Aureobasidium pullulans*,

*Sclerophoma*, such as *Sclerophoma pityophila*,

*Trichoderma*, such as *Trichoderma viride*,

*Escherichia*, such as *Escherichia coli*,

*Pseudomonas*, such as *Pseudomonas aeruginosa*, and

*Staphylococcus*, such as *Staphylococcus aureus*.

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can, as such or in their formulations, also be used in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Suitable mixing components are, for example, the following compounds:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulphamide, flutolanil; flutriafol; folpet; fosetyl-A1; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulphocarb; methfuroxam; metiram; metominostrobin; metsulphovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon;

pyroxyfur; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]-butanamide; 1-(1-naphthalenyl-1H-pyrrole-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-6-methoxy-3-pyridinyl)-cyclopropanecarboxamide; N-butyl-8-(1,1-dimethylethyl)-1-oxaspiro-[4.5]decane-3-amine; sodium tetrathiocarbonate; and copper salts and preparations, such as Bordeaux mixture; copper hydroxide; copper naphthenate; copper oxychloride; copper sulphate; cufraneb; copper oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulphan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cyclopene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methylsulphone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulphoton, docusat-sodium, dofenapyn, DOWCO-439, eflusilanate, emamectin, emamectin-benzoate, empenthrin (1R-isomer), endosulphan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulphothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulphenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S421, S-1833, salithion, sebufos, SI-0009, silafluofen, spinosad, spirodiclofen, spiromesifen, sulphluramid, sulphotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogenoxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, *Trichoderma atroviride*, triflumuron, trimethacarb, vamidothion, vaniliprole, verbutin, *Verticillium lecanii*, WL-108477, WL40027, YI-5201, YI-5301, YI-5302, XMC, xylylcarb, ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, safeners and/or semiochemicals is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi does by no means limit the mycotic spectrum which can be covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10000 g/ha, preferably between 1 and 5000 g/ha.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized are in particular increased defence of the plants against insects, arachnids, nematodes and slugs and snails by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The preparation and the use of the active compounds according to the invention is illustrated by the examples below.

PREPARATION EXAMPLES

Example 1

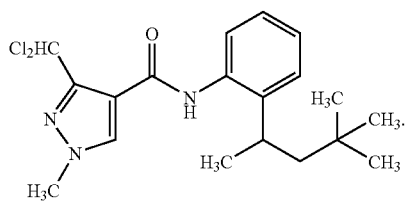

191.3 mg (1.0 mmol) of [2-(1,3,3-trimethylbutyl)phenyl]amine are added to a solution comprising 250.2 mg (1.1 mmol) of 3-dichloromethyl-1-methyl-1H-pyrazole-4-carbonyl chloride and 161.9 mg (1.6 mmol) of triethylamine in 10 ml of tetrahydrofuran. The reaction solution is stirred at 60° C. for 16 h, filtered through silica and concentrated under reduced pressure.

Column chromatography (cyclohexane/ethyl acetate 3:1) gives 342.1 mg (89% of theory) of 3-(dichloromethyl-1-methyl-N-[2-(1,3,3-trimethylbutyl)phenyl]-1H-pyrazole-4-carboxamide [logP (pH=2.3)=4.02].

The compounds of the formula (I) listed in Table 1 below are obtained analogously to Example 1 and in accordance with the instructions in the general descriptions of the processes.

TABLE 1

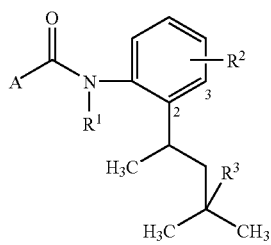

(I)

| Ex. | R¹ | R² | R³ | A | logP |
|---|---|---|---|---|---|
| 2 | H | H | CH₃ | (3,4,5-trimethyl-1H-pyrazol-4-yl) | 3.19 |

TABLE 1-continued

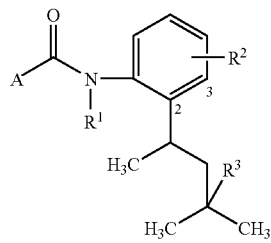

(I)

| Ex. | R¹ | R² | R³ | A | logP |
|---|---|---|---|---|---|
| 3 | H | H | CH₃ | (3-trifluoromethyl-4-methyl-5-chloro-1-methyl-1H-pyrazol-4-yl) | 4.34 |
| 4 | H | H | CH₃ | (3-ethyl-4-methyl-5-chloro-1-methyl-1H-pyrazol-4-yl) | 4.25 |
| 5 | H | H | CH₃ | (3-cyclopropyl-4-methyl-5-chloro-1-methyl-1H-pyrazol-4-yl) | 4.39 |
| 6 | H | H | CH₃ | (3-trifluoromethyl-4-methyl-1-methyl-1H-pyrazol-4-yl) | 3.81 |
| 7 | H | H | C₂H₅ | (3-trifluoromethyl-4-methyl-1-methyl-1H-pyrazol-4-yl) | 4.13 |
| 8 | H | H | CH₃ | (3-(1-fluoroethyl)-4-methyl-1-methyl-1H-pyrazol-4-yl) | 3.63 |

TABLE 1-continued
(I)
| Ex. | R¹ | R² | R³ | A | logP |
|---|---|---|---|---|---|
| 9 | H | H | CH₃ | 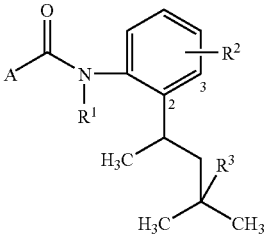 3-Cl, 4-CH₃, 1-CH₃ pyrazole | 3.79 |
| 10 | H | H | CH₃ | 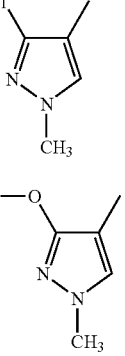 3-OCHF₂, 4-CH₃, 1-CH₃ pyrazole | 4.19 |
| 11 | H | H | CH₃ | 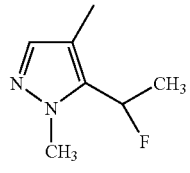 4-CH₃, 5-CHFCH₃, 1-CH₃ pyrazole | 3.81 |
| 12 | H | H | CH₃ | 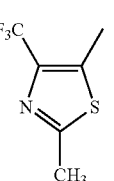 4-CF₃, 5-CH₃, 2-CH₃ thiazole | 4.24 |
| 13 | H | H | CH₃ | 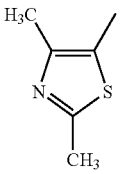 4-CH₃, 5-CH₃, 2-CH₃ thiazole | 3.60 |
| 14 | H | H | CH₃ | 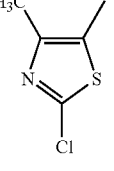 4-CH₃, 5-CH₃, 2-Cl thiazole | 4.52 |
| 15 | H | H | C₂H₅ | 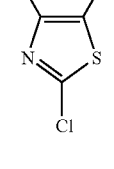 4-CH₃, 5-CH₃, 2-Cl thiazole | 4.89 |
TABLE 1-continued
(I)
| Ex. | R¹ | R² | R³ | A | logP |
|---|---|---|---|---|---|
| 16 | H | H | CH₃ | 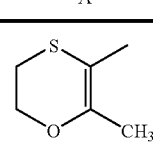 | 4.27 |
| 17 | H | H | C₂H₅ | 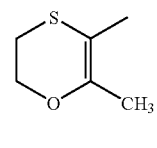 | 4.63 |
| 18 | H | H | CH₃ | 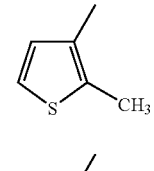 | 4.39 |
| 19 | H | H | CH₃ | 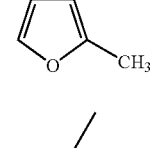 | 4.04 |
| 20 | H | H | C₂H₅ | 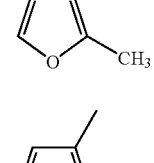 | 4.38 |
| 21 | H | H | CH₃ | 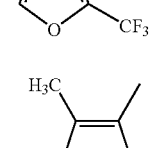 | 4.37 |
| 22 | H | H | CH₃ | 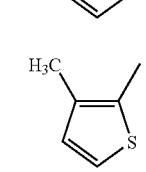 | 4.40 |
| 23 | H | H | C₂H₅ | 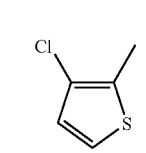 | 4.75 |
| 24 | H | H | CH₃ |  | 4.92 |

TABLE 1-continued (I)

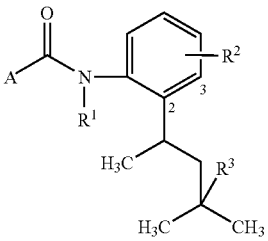

| Ex. | R¹ | R² | R³ | A | logP |
|---|---|---|---|---|---|
| 25 | H | H | CH₃ | 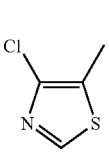 | 3.84 |
| 26 | H | H | CH₃ | 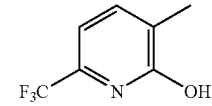 | 4.15 |
| 27 | H | H | CH₃ | 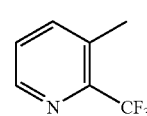 | 3.97 |
| 28 | H | H | CH₃ | 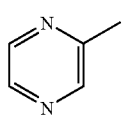 | 3.89 |
| 29 | H | H | CH₃ | 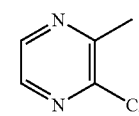 | 3.97 |
| 30 | H | H | CH₃ | 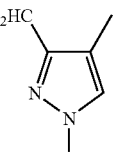 | 3.95 |
| 31 | H | H | CH₃ | 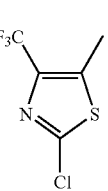 | 4.16 |
| 32 | H | H | CH₃ | 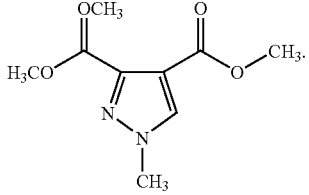 | 4.80 |

Preparation of Starting Materials of the Formula (II)

Example (II-1)

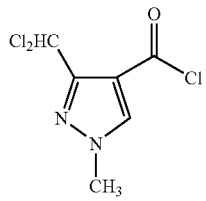

300.0 mg (1.9 mmol) of 3-formyl-1-methyl-1H-pyrazole-4-carboxylic acid are dissolved in 60 ml of dichloromethane, and 1.0 g (4.9 mmol) of phosphorus pentachloride is added. After 1.5 h at room temperature, the mixture is poured onto ice-water and extracted with dichloromethane, and the extracts are dried over magnesium sulphate, filtered and concentrated under reduced pressure.

This gives 384.0 mg (86% of theory) of 3-dichloromethyl-1-methyl-1H-pyrazole-4-carbonyl chloride [logP (pH 2.3)=1.80].

Preparation of Starting Materials of the Formula (VII)

Example (VII-1)

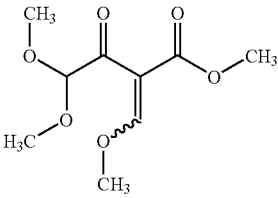

16.0 ml (170 mol) of acetic anhydride are added to a solution comprising 10.0 g (57 mmol) of methyl 4,4-dimethoxy-3-oxobutyrate in 9.0 g (85 mmol) of trimethyl orthoformate. The reaction mixture is heated under reflux for 16 h.

Distillation of the reaction mixture (boiling point 132-135° C., 0.2 bar) gives 7.0 g (56% of theory) of methyl 4,4-dimethoxy-2-methoxymethylene-3-oxobutyrate.

Preparation of Starting Materials of the Formula (IX)

Example (IX-1)

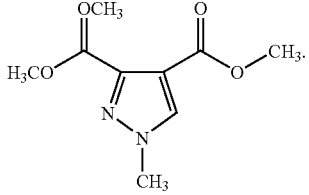

At −5° C., a solution comprising 2.0 ml (38 mmol) of methylhydrazine in 340 ml of methanol is slowly added dropwise to 7.5 g of methyl 4,4-dimethoxy-2-methoxymethylene-3-oxobutyrate. After the addition has ended, the reaction mixture is stirred at room temperature for 16 h and concentrated under reduced pressure.

Column chromatography (mobile phase gradient cyclohexane/ethyl acetate) gives 6.5 g (77% of theory) of methyl 3-dimethoxymethyl-1-methyl-1H-pyrazole-4-carboxylate.

Preparation of Starting Materials of the Formula (X)

Example (X-1)

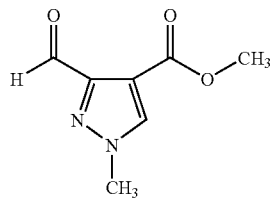

10 ml of concentrated hydrochloric acid is added to a solution of 2.1 g (10 mmol) of methyl 3-dimethoxymethyl-1-methyl-1H-pyrazole-4-carboxylate in 20 ml of dioxane, and the mixture is stirred at room temperature for 1.6 h. For work-up, the mixture is concentrated under reduced pressure and the residue is taken up in 200 ml of methylene chloride and washed with 50 ml of water. The organic phase is dried over magnesium sulphate, filtered and concentrated.

This gives 1.6 g (94% of theory) of methyl 3-formyl-1-methyl-1H-pyrazole-4-carboxylate [logP (pH 2.3)=0.46].

Preparation of Starting Materials of the Formula (XI)

Example (XI-1)

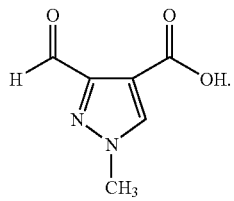

6.0 g (35.68 mmol) of methyl 3-formyl-1-methyl-1H-pyrazole-4-carboxylate are dissolved in 180 ml of tetrahydrofuran and 90 ml of water, and 0.94 g (39.25 mmol) of lithium hydroxide is added. The reaction mixture is stirred at room temperature for 16 h, the organic solvent is removed under reduced pressure and the aqueous phase that remains is acidified with dilute hydrochloric acid and extracted three times with in each case 100 ml of ethyl acetate. The organic phases are dried over magnesium sulphate, filtered and concentrated.

This gives 4.28 g (78% of theory) of 3-formyl-1-methyl-1H-pyrazole-4-carboxylic acid of logP (pH=2.3)=−0.19.

Preparation of Starting Materials of the Formula (XII)

Example (XII-1)

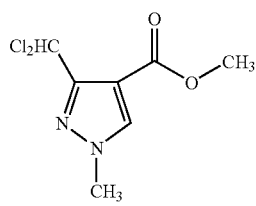

46.1 mg (0.27 mmol) of methyl 3-formyl-1-methyl-1H-pyrazole-4-carboxylate are dissolved in 10 ml of dichloromethane, and 142.9 mg (0.67 mmol) of phosphorus pentachloride are added. The reaction mixture is stirred at room temperature for 1.5 h, added to water and extracted with diethyl ether, and the extract is dried over magnesium sulphate and concentrated under reduced pressure.

This gives 53.0 mg (86% of theory) of methyl 3-(dichloromethyl)-1-methyl-1H-pyrazole-4-carboxylate of logP (pH 2.3)=1.80.

This methyl ester can be hydrolysed in the customary manner. This gives 3-(dichloromethyl)-1-methyl-1H-pyrazole-4-carboxylic acid which is coupled with compounds of the formula (III) either directly or after conversion into the acid chloride.

The determination of the logP values given in the preparation examples and tables above is carried out in accordance with EEC Directive 79/831 Annex V.A8 by HPLC (High Performance Liquid Chromatography) on a reversed-phase column (C 18). Temperature: 43° C.

The determination is carried out in the acidic range at pH 2.3 using the mobile phases, 0.1% aqueous phosphoric acid and acetonitrile; linear gradient from 10% acetonitrile to 90% acetonitrile.

Calibration is carried out using unbranched alkan-2-ones (of 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

USE EXAMPLES

Example A

*Podosphaera* Test (Apple)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of the apple mildew pathogen *Podosphaera leucotricha*. The plants are then placed in a greenhouse at about 23° C. and a relative atmospheric humidity of about 70%.

Evaluation is carried out 10 days after the inoculation. 0% means an efficacy which corresponds to that of the control, whereas an efficacy of 100% means that no infection is observed.

TABLE A
Podosphaera test (apple)/protective
| Active compound According to the invention | Application rate of active compound in g/ha | Efficacy in % |
|---|---|---|
| 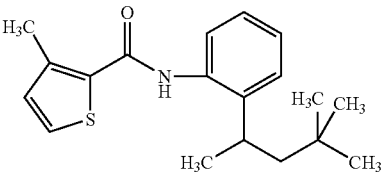 | 100 | 85 |
| 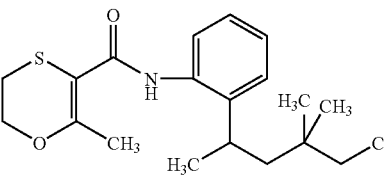 | 100 | 94 |
| 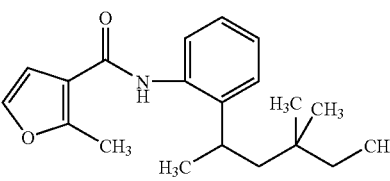 | 100 | 91 |
| 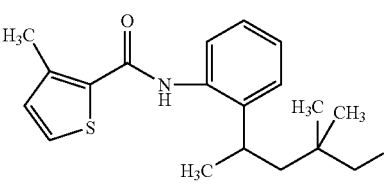 | 100 | 98 |
| 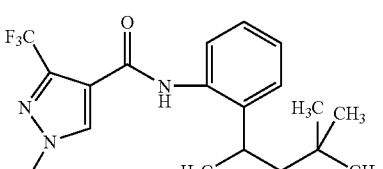 | 100 | 95 |
| 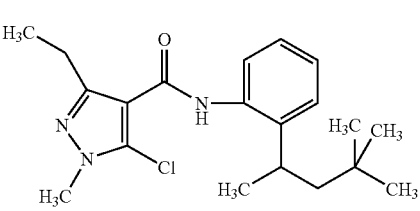 | 100 | 96 |
| 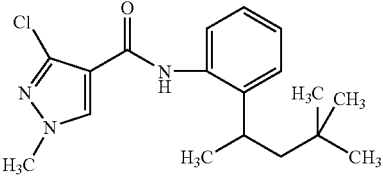 | 100 | 100 |

TABLE A-continued

Podosphaera test (apple)/protective

| Active compound According to the invention | Application rate of active compound in g/ha | Efficacy in % |
|---|---|---|
| [Structure: 1-methyl-3-trifluoromethyl-5-chloro-pyrazole-4-carboxamide with 2-(2,4,4-trimethylpentan-2-yl)phenyl substituent] | 100 | 97 |
| [Structure: 2-methyl-4-trifluoromethyl-thiazole-5-carboxamide with 2-(2,4,4-trimethylpentan-2-yl)phenyl substituent] | 100 | 100 |

Example B

Venturia Test (Apple)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

TABLE B

Venturia test (apple)/protective

| Active compound According to the invention | Application rate of active compound in g/ha | Efficacy in % |
|---|---|---|
| [Structure: 3-methylthiophene-2-carboxamide with 2-(2,4,4-trimethylpentan-2-yl)phenyl substituent] | 100 | 96 |
| [Structure: 3-methyl-5,6-dihydro-1,4-oxathiine-2-carboxamide with 2-(tert-butyl-methyl-methyl)phenyl substituent] | 100 | 100 |
| [Structure: 3-methyl-5,6-dihydro-1,4-oxathiine-2-carboxamide with 2-(2,2-dimethylpentan-3-yl)phenyl substituent] | 100 | 100 |

TABLE B-continued
Venturia test (apple)/protective
| Active compound According to the invention | Application rate of active compound in g/ha | Efficacy in % |
|---|---|---|
| 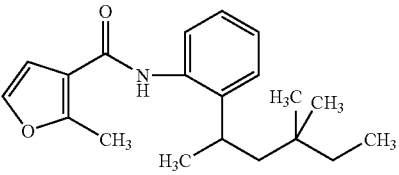 | 100 | 93 |
| 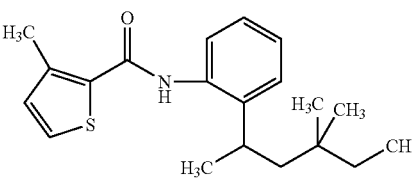 | 100 | 99 |
| 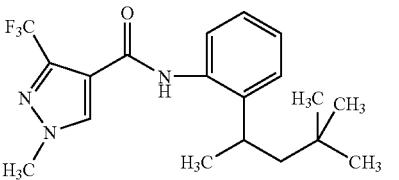 | 100 | 95 |
| 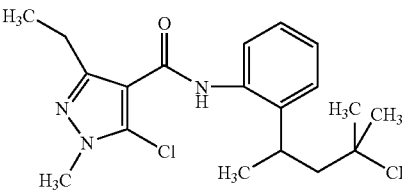 | 100 | 92 |
| 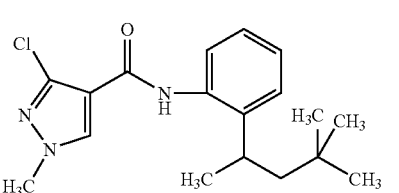 | 100 | 100 |
| 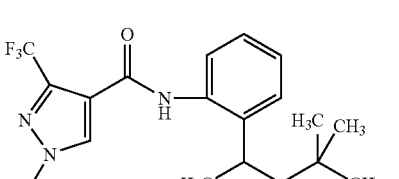 | 100 | 99 |
| 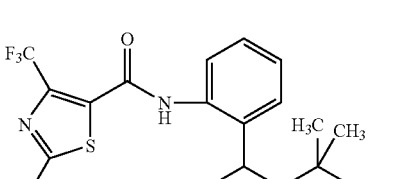 | 100 | 99 |

Example C

Botrytis Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by Botrytis cinerea are placed onto each leaf. The inoculated plants are placed in a dark chamber at about 20° C. and 100% relative atmospheric humidity.

2 days after the inoculation, the size of the infected areas on the leaves is evaluated. 0% means an efficacy which corresponds to that of the control, whereas an efficacy of 100% means that no infection is observed.

TABLE C

Botrytis test (bean)/protective

| Active compound According to the invention | Application rate of active compound in g/ha | Efficacy in % |
|---|---|---|
| [structure] | 500 | 100 |
| [structure] | 500 | 95 |
| [structure] | 500 | 100 |
| [structure] | 500 | 88 |
| [structure] | 500 | 100 |
| [structure] | 500 | 100 |

TABLE C-continued

Botrytis test (bean)/protective

| Active compound According to the invention | Application rate of active compound in g/ha | Efficacy in % |
|---|---|---|
| [Structure: 3-chloro-1-methylpyrazole-4-carboxamide with 2-(2,3-dimethylbutan-2-yl... neopentyl-type)phenyl group] | 500 | 95 |
| [Structure: 3-trifluoromethyl-1-methylpyrazole-4-carboxamide with same aryl group] | 500 | 97 |
| [Structure: 2-methyl-4-trifluoromethylthiazole-5-carboxamide with same aryl group] | 500 | 95 |

Example D

Puccinia Test (Wheat)/Curative a) Solvent: 50 parts by weight of N,N-dimethylacetamide
   Emulsifier: 1 part by weight of alkylaryl polyglycol ether
b) Solvent: 25 parts by weight of N,N-dimethylacetamide
   Emulsifier: 0.6 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

TABLE D

Puccinia test (wheat)/protective

| Active compound According to the invention | Application rate of active compound in g/ha | Efficacy in % | Solvent/ emulsifier |
|---|---|---|---|
| [Structure: 2,4-dimethylthiazole-5-carboxamide with 2-(2,3-dimethylbutan-2-yl-type neopentyl) phenyl group] | 500 | 100 | a) |

TABLE D-continued

Puccinia test (wheat)/protective

| Active compound According to the invention | Application rate of active compound in g/ha | Efficacy in % | Solvent/ emulsifier |
|---|---|---|---|
| [structure] | 500 | 100 | a) |
| [structure] | 500 | 100 | a) |
| [structure] | 500 | 100 | a) |
| [structure] | 500 | 100 | a) |
| [structure] | 500 | 100 | a) |
| [structure] | 500 | 100 | b) |
| [structure] | 500 | 100 | b) |

TABLE D-continued

Puccinia test (wheat)/protective

| Active compound<br>According to the invention | Application rate of active compound in g/ha | Efficacy in % | Solvent/emulsifier |
|---|---|---|---|
| 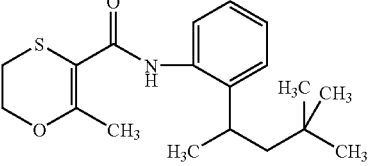 | 500 | 100 | b) |
| 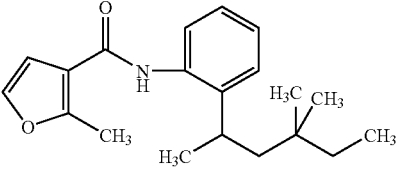 | 500 | 100 | b) |

Example E

*Sphaerotheca* Test (Cucumber)/Protective

Solvent: 49 parts by weight of N,N-dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young cucumber plants are sprayed with the preparation of active compound at the stated application rate. 1 day after treatment the plants are inoculated with a spore suspension of *Sphaerotheca fuliginea*. The plants are then placed in a greenhouse at a relative atmospheric humidity of 70% and a temperature of 23° C.

Evaluation is carried out 7 days after the inoculation. 0% means an efficacy which corresponds to that of the control, whereas an efficacy of 100% means that no infection is observed.

TABLE E

Sphaerotheca test (cucumber)/protective

| Active compound<br>According to the invention | Application rate of active compound in g/ha | Efficacy in % |
|---|---|---|
| 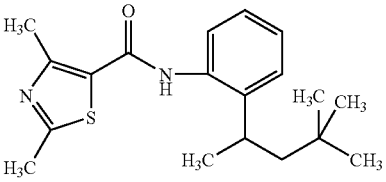 | 750 | 95 |
| 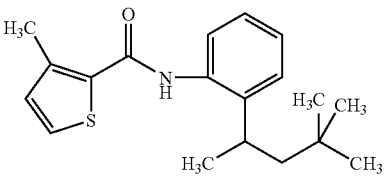 | 750 | 95 |
| 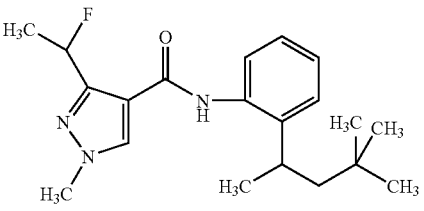 | 750 | 90 |

Example F

Erysiphe Test (Barley)/Protective

Solvent: 25 parts by weight of N,N-dimethylacetamide

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of Erysiphe graminis f.sp. hordei.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

TABLE F

Erysiphe test (barley)/protective

| Active compound According to the invention. | Application rate of active compound in g/ha | Efficacy in % |
|---|---|---|
| 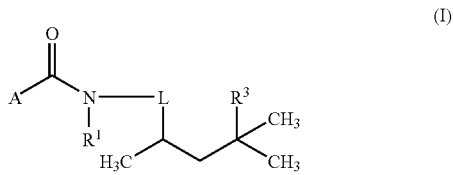 | 500 | 100 |
| 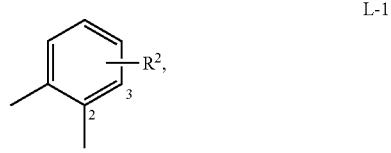 | 500 | 100 |
| 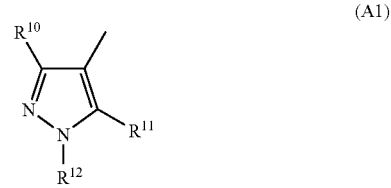 | 500 | 94 |
| (structure) | 500 | 100 |

TABLE F-continued

Erysiphe test (barley)/protective

| Active compound According to the invention. | Application rate of active compound in g/ha | Efficacy in % |
|---|---|---|
| 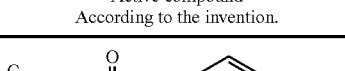 | 500 | 100 |

What is claimed is:

1. A hexylcarboxanilide of formula (I)

(I)

in which

L represents

L-1

$R^1$ represents hydrogen, $C_1$-$C_8$-alkyl, or $C_1$-$C_6$-haloalkyl, $R^2$ represents hydrogen, fluorine, chlorine, methyl, or trifluoromethyl, $R^3$ represents $C_1$-$C_8$-alkyl or $C_1$-$C_8$-haloalkyl, and A represents a radical of formula (A1)

(A1)

in which $R^{10}$ represents hydrogen, hydroxyl, formyl, cyano, fluorine, chlorine, bromine, nitro, $C_1$-$C_4$-alkyl, $C_1$-$C_4$-alkoxy, $C_1$-$C_4$-alkylthio, or $C_3$-$C_6$-cycloalkyl; represents $C_1$-$C_4$-haloalkyl, $C_1$-$C_4$-haloalkoxy, or $C_1$-$C_4$-haloalkylthio having in each case 1 to 5 halogen atoms; or represents aminocarbonyl or aminocarbonyl-$C_1$-$C_4$-alkyl, $R^{11}$ represents hydrogen, chlorine, bromine, iodine, cyano, $C_1$-$C_4$-alkyl, $C_1$-$C_4$-alkoxy, or $C_1$-$C_4$-alkylthio; or represents $C_1$-$C_4$-haloalkyl or $C_1$-$C_4$-haloalkylthio having in each case 1 to 5 halogen atoms, and $R^{12}$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$- or alkoxy-$C_1$-$C_4$-alkyl; represents $C_1$-$C_4$-haloalkyl, $C_1$-$C_4$-haloalkylthio-$C_1$-$C_4$-alkyl or $C_1$-$C_4$-haloalkoxy-$C_1$-$C_4$-alkyl having in each case 1 to 5 halogen atoms; or represents phenyl.

2. A hexylcarboxanilide of formula (I) according to claim 1 in which

L represents

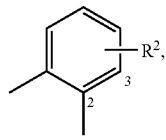

L-1

$R^1$ represents hydrogen, $C_1$-$C_6$-alkyl, or $C_1$-$C_4$-haloalkyl,
$R^2$ represents hydrogen, fluorine, chlorine, methyl, or trifluoromethyl,
$R^3$ represents $C_1$-$C_6$-alkyl or $C_1$-$C_6$-halo-alkyl having in each case 1 to 13 fluorine, chlorine, and/or bromine atoms, and
A represents a radical of formula (A1)

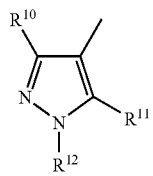

(A1)

in which $R^{10}$ represents hydrogen, hydroxyl, formyl, cyano, fluorine, chlorine, bromine, methyl, ethyl, isopropyl, methoxy, ethoxy, methylthio, ethylthio, or cyclopropyl; represents $C_1$-$C_2$-haloalkyl or $C_1$-$C_2$-haloalkoxy having in each 1 to 5 fluorine, chlorine, and/or bromine atoms; or represents trifluoromethylthio, difluoromethylthio, aminocarbonyl, aminocarbonylmethyl, or aminocarbonylethyl, $R^{11}$ represents hydrogen, chlorine, bromine, iodine, methyl, ethyl, methoxy, ethoxy, methylthio, ethylthio, or $C_1$-$C_2$-haloalkyl having 1 to 5 fluorine, chlorine, and/or bromine atoms, and $R^{12}$ represents hydrogen, methyl, ethyl, n-propyl, isopropyl, $C_1$-$C_2$-haloalkyl having 1 to 5 fluorine, chlorine, and/or bromine atoms, hydroxymethyl, hydroxyethyl, cyclopropyl, cyclopentyl, cyclohexyl, or phenyl.

3. A hexylcarboxanilide of formula (I) according to claim 1 in which $R^1$ represents hydrogen.

4. A hexylcarboxanilide of formula (I) according to claim 1 in which $R^3$ represents $C_1$-$C_8$-alkyl.

5. A hexylcarboxanilide of formula (I) according to claim 1 in which $R^3$ represents $C_1$-$C_8$-haloalkyl.

6. A composition comprising one or more hexylcarboxanilides of formula (I) according to claim 1 and one or more extenders and/or surfactants.

7. A method of controlling fungi comprising applying an effective amount of one or more hexylcarboxanilides of formula (I) according to claim 1 to the fungi and/or their habitats.

* * * * *